(12) United States Patent
Cain et al.

(10) Patent No.: US 8,828,719 B2
(45) Date of Patent: Sep. 9, 2014

(54) METHOD FOR PRODUCING PROTEIN

(75) Inventors: Katharine Lacy Cain, Slough (GB); Shirley Jane Peters, Slough (GB); Paul Edward Stephens, Slough (GB)

(73) Assignee: UCB Pharma, S.A., Brussels (BE)

( * ) Notice: Subject to any disclaimer, the term of this patent is extended or adjusted under 35 U.S.C. 154(b) by 277 days.

(21) Appl. No.: 13/148,740

(22) PCT Filed: Feb. 10, 2010

(86) PCT No.: PCT/GB2010/000234
§ 371 (c)(1),
(2), (4) Date: Nov. 30, 2011

(87) PCT Pub. No.: WO2010/092335
PCT Pub. Date: Aug. 19, 2010

(65) Prior Publication Data
US 2012/0094297 A1    Apr. 19, 2012

(30) Foreign Application Priority Data
Feb. 10, 2009   (GB) .................................. 0902180.9

(51) Int. Cl.
*C12N 15/85* (2006.01)
*C12N 15/63* (2006.01)

(52) U.S. Cl.
USPC .......... 435/325; 435/320.1; 435/455

(58) Field of Classification Search
None
See application file for complete search history.

(56) References Cited
U.S. PATENT DOCUMENTS
8,034,607 B2 * 10/2011 Shusta et al. ............... 435/254.2

FOREIGN PATENT DOCUMENTS

| WO | 99/07727 A1 | 2/1999 |
|----|----|----|
| WO | 03/089622 A2 | 10/2003 |
| WO | 2004/111194 A2 | 12/2004 |
| WO | 2006/028889 A2 | 3/2006 |
| WO | 2006/067511 A2 | 6/2006 |
| WO | 2008/115596 A2 | 9/2008 |

OTHER PUBLICATIONS

Mezchrani, et al, "Manipulation of oxidative protein folding an PDI redox state in mammalian cells," The Embo Journal, Nov. 15, 2001, LNKD-PUBMED:11707400, vol. 20, No. 22, pp. 6288-6296.
Yoshida, H., et al, "XBPI mRNA is induced by ATF6 and spliced by IRE1 in response to ER stress to produe a highly active transcription factor," Cell, Cell Press, Cambridge, NA, US LNKD-DOI:10.1016/S0092-8674(01)00611-O, vol. 107, Dec. 28, 2001, pp. 881-891.
Lee, Ann-Hwee, et al, "XBP-1 regulates a subset of endoplasmic reticulum resident chaperone genes in the unfolded protein response," Molecular and Cellular Biology, Nov. 2003, LNKD-PUBMED:14559994, vol. 23, No. 21, pp. 7448-7459.
Gunn, K.E., et al, "A role for the unfolded protein response in optimizing antibody secretion", Molecular Immunology, Pergamon, GB LNKD-DOI:10.1016/J.MOLIMM.2004.04.023, vol. 41, Jun. 5, 2004, pp. 919-927.
Tigges, M., et al, "Xbp1-based engineering of secretory capacity enhances the productivity of Chinese hamster ovary cells," Metabolic Engineering, Academic Press, US LNKD-DOI:10.1016/J.YMBEN.2006.01.006, vol, 8, No. 3, May 1, 2006, pp. 264-272.

* cited by examiner

*Primary Examiner* — Celine Qian
(74) *Attorney, Agent, or Firm* — McDonnell Boehnen Hulbert & Berghoff LLP

(57) ABSTRACT

The present invention relates to a recombinant host cell, wherein the cell is modified to increase the expression levels of Ero1 and XBP1 relative to the expression levels of Ero1 and XBP1 in an unmodified cell. The present invention also relates to a method of producing a recombinant protein of interest comprising expressing the recombinant protein of interest in the recombinant host cell.

27 Claims, 17 Drawing Sheets

Figure 1

(a)  Amino acid sequence of the spliced form of human XBP1 (SEQ ID NO: 1)

MVVVAAAPNPADGTPKVLLLSGQPASAAGAPAGQALPLMVPAQRGASPEAASGG
LPQARKRQRLTHLSPEEKALRRKLKNRVAAQTARDRKKARMSELEQQVVDLEEE
NQKLLLENQLLREKTHGLVVENQELRQRLGMDALVAEEEAEAKGNEVRPVAGSA
ESAAGAGPVVTPPEHLPMDSGGIDSSDSESDILLGILDNLDPVMFFKCPSPEPASLEE
LPEVYPEGPSSLPASLSLSVGTSSAKLEAINELIRFDHIYTKPLVLEIPSETESQANVV
VKIEEAPLSPSENDHPEFIVSVKEEPVEDDLVPELGISNLLSSSHCPKPSSCLLDAYS
DCGYGGSLSPFSDMSSLLGVNHSWEDTFANELFPQLISV*

(b)  Nucleic acid sequence of the spliced form of human XBP1 (SEQ ID NO: 2)

atggtggtggtggcagccgcgccgaacccggccgacgggaccccctaaagttctgcttctgtcggggcagcccgcctccgccgc
cggagccccggccggccaggccctgccgctcatggtgccagcccagagaggggccagcccggaggcagcgagcgggggg
ctgccccaggcgcgcaagcgacagcgcctcacgcacctgagccccgaggagaaggcgctgaggaggaaactgaaaaacaga
gtagcagctcagactgccagagatcgaaagaaggctcgaatgagtgagctggaacagcaagtggtagatttagaagaagagaa
ccaaaaacttttgctagaaaatcagcttttacgagagaaaactcatggccttgtagttgagaaccaggagttaagacagcgcttggg
gatggatgccctggttgctgaagaggaggcggaagccaaggggaatgaagtgaggccagtggccgggtctgctgagtccgca
gcaggtgcaggcccagttgtcacccctccagaacatctcccatggattctggcggtattgactcttcagattcagagtctgatatcc
tgttgggcattctggacaacttggacccagtcatgttcttcaaatgcccttccccagagcctgccagcctggaggagctcccagagg
tctacccagaaggacccagttccttaccagcctccctttctctgtcagtggggacgtcatcagccaagctggaagccattaatgaact
aattcgttttgaccacatatataccaagcccctagtcttagagatacctctgagacagagagccaagctaatgtggtagtgaaaatc
gaggaagcacctctcagcccctcagagaatgatcaccctgaattcattgtctcagtgaaggaagaacctgtagaagatgacctcgtt
ccggagctgggtatctcaaatctgctttcatccagccactgcccaaagccatcttcctgcctactggatgcttacagtgactgtggata
cggggggttccctttccccattcagtgacatgtcctctctgcttggtgtaaaccattcttgggaggacacttttgccaatgaactctttccc
cagctgattagtgtctaa

Figure 2

(a) Amino acid sequence of human Ero1alpha (SEQ ID NO: 3)

MGRGWGFLFGLLGAVWLLSSGHGEEQPPETAAQRCFCQVSGYLDDCTCDVETID
RFNNYRLFPRLQKLLESDYFRYYKVNLKRPCPFWNDISQCGRRDCAVKPCQSDEV
PDGIKSASYKYSEEANNLIEECEQAERLGAVDESLSEETQKAVLQWTKHDDSSDNF
CEADDIQSPEAEYVDLLLNPERYTGYKGPDAWKIWNVIYEENCFKPQTIKRPLNPL
ASGQGTSEENTFYSWLEGLCVEKRAFYRLISGLHASINVHLSARYLLQETWLEKK
WGHNITEFQQRFDGILTEGEGPRRLKNLYFLYLIELRALSKVLPFFERPDFQLFTGN
KIQDEENKMLLLEILHEIKSFPLHFDETSFFAGDKKEAHKLKEDFRLHFRNISRIMD
CVGCFKCRLWGNLQTQGLGTALKILFSEKLIANMPESGPSYEFHLTRQEIVSLFNAF
GRISTSVKELENFRNLLQNIH*

(b) Nucleic acid sequence of human Ero1alpha (SEQ ID NO: 4)

atgggccgcggctggggattcttgtttggcctcctgggcgccgtgtggctgctcagctcgggccacggagaggagcagcccccg
gagacagcggcacagaggtgcttctgccaggttagtggttacttggatgattgtacctgtgatgttgaaaccattgatagatttaataa
ctacaggcttttcccaagactacaaaaacttcttgaaagtgactactttaggtattacaaggtaaacctgaagaggccgtgtcctttctg
gaatgacatcagccagtgtggaagaagggactgtgctgtcaaaccatgtcaatctgatgaagttcctgatggaattaaatctgcgag
ctacaagtattctgaagaagccaataatctcattgaagaatgtgaacaagctgaacgacttggagcagtggatgaatctctgagtga
ggaaacacagaaggctgttcttcagtggaccaagcatgatgattcttcagataacttctgtgaagctgatgacattcagtcccctgaa
gctgaatatgtagatttgcttcttaatcctgagcgctacactggttacaaggggaccagatgcttggaaaatatggaatgtcatctacga
agaaaactgttttaagccacagacaattaaaagaccttttaaatcctttggcttctggtcaagggacaagtgaagagaacacttttttaca
gttggctagaaggtctctgtgtagaaaaaagagcattctacagacttatatctggcctacatgcaagcattaatgtgcatttgagtgca
agatatcttttacaagagacctggttagaaaagaaatggggacacaacattacagaatttcaacagcgatttgatggaattttgactga
aggagaaggtccaagaaggcttaagaacttgtattttctctacttaatagaactaagggctttatccaaagtgttaccattcttcgagcg
cccagattttcaactctttactggaaataaaattcaggatgaggaaaacaaaatgttacttctggaaatacttcatgaaatcaagtcattt
cctttgcattttgatgagacttcattttttgctggggataaaaaagaagcacacaaactaaaggaggactttcgactgcattttagaaat
atttcaagaattatggattgtgttggttgttttaaatgtcgtctgtggggaaatcttcagactcagggtttgggcactgctctgaagatctt
attttctgagaaattgatagcaaatatgccagaaagtggacctagttatgagttccatctaaccagacaagaaatagtatcattattcaa
cgcatttggaagaatttctacaagtgtgaaagaattagaaaacttcaggaacttgttacagaatatcattaa mAb 42

1. CHOS
2. CHOSX
3. CHOSXE
4. CHOK1

Reduced     Non-Reduced mAb 61

1. CHOS
2. CHOSX
3. CHOSXE
4. CHOK1

Reduced     Non-Reduced mAb 164

1. CHOS
2. CHOSX
3. CHOSXE
4. CHOK10

Reduced    Non-Reduced

Figure 14

|  | | mAb 42 | | mAb 61 | | mAb 164 | | | Average | |
|---|---|---|---|---|---|---|---|---|---|---|
|  | | CHOS | CHOS XE | CHOS | CHOS XE | CHOS | CHOS XE | | CHOS | CHOS XE |
|  | G0F | 47 | 53 | 37 | 48 | 49 | 50 | | 44 | 50 |
|  | G1F | 21 | 10 | 17 | 11 | 24 | 18 | | 21 | 13 |
|  | G2F | 2 | 0 | 1 | 0 | 1 | 1 | | 2 | 1 |
|  | M3N3F | 1 | 1 | 1 | 2 | 1 | 2 | | 1 | 2 |
|  | M3N2F | 1 | 0 | 0 | 0 | 0 | 0 | | 0 | 0 |
|  | G0 | 7 | 22 | 11 | 26 | 10 | 16 | | 9 | 21 |
|  | G1 | 9 | 5 | 17 | 5 | 6 | 8 | | 11 | 6 |
|  | G2 | 0 | 1 | 6 | 1 | 2 | 1 | | 3 | 1 |
|  | M3N3 | 0 | 3 | 1 | 1 | 0 | 2 | | 0 | 2 |
|  | M3N2 | 1 | 0 | 1 | 0 | 0 | 0 | | 0 | 0 |
|  | M5 | 9 | 5 | 8 | 5 | 6 | 2 | | 8 | 4 |
|  | M6 | 2 | 1 | 0 | 0 | 0 | 0 | | 1 | 0 |
|  | M7 | 0 | 0 | 0 | 0 | 0 | 0 | | 0 | 0 |
|  | M8 | 0 | 0 | 0 | 0 | 0 | 0 | | 0 | 0 |
|  | M9 | 0 | 0 | 0 | 0 | 0 | 0 | | 0 | 0 |
| Fucosylated | | 72 | 65 | 55 | 62 | 76 | 71 | | 68 | 66 |
| Non-fucosylated | | 17 | 30 | 36 | 33 | 18 | 27 | | 24 | 30 |
| High mannose | | 11 | 5 | 9 | 5 | 6 | 2 | | 9 | 4 |

METHOD FOR PRODUCING PROTEIN

This application is a US national phase of International Application No. PCT/GB2010/000234 filed on Feb. 10, 2010, which claims the benefit of Great Britain patent application 0902180.9, filed Feb. 10, 2009, the disclosures of which are incorporated herein by reference in their entirety.

The present invention relates to a recombinant host cell capable of improved production of a protein of interest. The invention also relates to a method for improving the capability of a cell to produce a protein of interest and a method for producing a protein of interest in such a cell.

BACKGROUND OF THE INVENTION

One of the most important functions of endoplasmic reticulum (ER)-Golgi system is to facilitate post-translational modifications including protein folding. The correct folding of newly-translated proteins is essential for secreted extracellular proteins and membrane proteins to ensure that they can function correctly. Protein folding allows a polypeptide to fold into its characteristic and functional three-dimensional structure. Protein folding involves the formation of both non-covalent and covalent bonds. Generally in eukaryotic cells, protein folding is mediated in the rough ER by ER chaperone proteins.

Protein disulphide isomerase (PDI) is a chaperone protein which catalyzes the formation and isomerisation of disulphide bonds between two cysteine residues in polypeptides. The formation of disulphide bonds is a redox reaction. Proteins are oxidized by PDI when it is in an oxidized state, which produces a disulphide bond in the protein and renders PDI in a reduced state comprising free sulfhydryl groups.

ER oxidoreductin 1 protein (Ero1) is an essential component of oxidative folding machinery. Ero1 is a flavin adenine dinucleotide (FAD) dependent enzyme which facilitates disulphide bond formation in immunoglobulin subunits by selectively oxidizing PDI (Mezghrani et al., 2001, EMBO Journal, 20(22), 6288-6296). In humans two isoforms have been identified as human Ero1-Lα and Ero1-Lβ.

U.S. Pat. No. 6,361,964 discloses expression systems that make use of Ero1 to enhance disulphide bond formation and thereby to increase the yield of properly folded recombinant proteins.

The unfolded protein response (UPR) allows cells to respond to an increased demand on the protein folding capacity of the ER by coordinating the down regulation of protein synthesis with the increased expression of various proteins including ER resident chaperone proteins and folding enzymes which enable protein folding (Gunn et al., 2004, Molecular Immunology, 41, 919-9927). The UPR may also cause enlargement of the ER in order to provide increased capacity for protein folding.

X Box Binding Protein 1 (XBP1) is known to be a key regulator of the unfolded protein response. XBP1 is a transcription factor which is involved in B cell differentiation, ER expansion by stimulating activity of enzymes involved in lipid biosynthesis and regulates gene encoding ER resident chaperone proteins involved in the UPR (Lee et al., 2003, Molecular and Cellular Biology, 23(21), 7448-7459). XBP1 is believed to cause enlargement of the ER by up-regulating or activating enzymes including choline cytidylyltransferase (CCT). CCT is the rate-limiting enzyme in the CDP-choline pathway for the production of phosphatidylcholine (PtdCho), which is the primary phospholipid of the ER membrane.

The use of XBP1 in methods for protein production wherein a protein of interest is co-expressed with XBP1 are described in WO 2004/111194, WO 2006/028889 and US2005/0250182.

Accordingly, methods to improve the yield of protein expression systems using a component of the UPR pathway are known. However, there is still a need to provide improved methods for increasing the yield of proteins in expression systems.

SUMMARY OF THE INVENTION

The present invention provides a recombinant host cell capable of improved yield of a protein of interest. The present inventors have demonstrated that an increase of both Ero1 and XBP1 in a cell provides improved means for providing a protein of interest.

Hence, the present invention provides a recombinant host cell, wherein the cell is modified to increase expression levels of Ero1 and XBP1 relative to the expression levels of Ero1 and XBP1 in an unmodified cell.

The present invention also provides a cell comprising an agent suitable for increasing the levels of Ero1 and XBP1 in the cell. Any suitable agent may be used for increasing the levels of Ero1 and XBP1. Typically the agent is one or more exogenous polynucleotide sequences encoding Ero1 and XBP1. Accordingly, the present invention provides a cell comprising one or more exogenous polynucleotide sequences encoding Ero1 and XBP1. A further typical agent may be capable of modulating endogenous polynucleotides encoding Ero1 and XBP1 in order to increase Ero1 and XBP1 expression. Accordingly, the present invention also provides a cell comprising an agent capable of increasing endogenous Ero1 and XBP1 expression.

The cell provided by the present invention is advantageous because in one embodiment it increases the yield of a protein of interest. In a further embodiment the present method increases the cell's capacity to perform post-translational modifications. The present method may initiate or up-regulate the UPR pathway. Further, the protein of interest expressed by the cell according to the present invention may have substantially the same properties as when the protein is expressed by an unmodified cell.

The present invention also provides a method comprising modifying a cell to thereby increase the capability of the cell to increase the expression levels of Ero1 and XBP1 relative to the expression levels of Ero1 and XBP1 in an unmodified cell.

In one aspect of the present invention the method is for expressing a protein of interest. The present inventors have found that the over expression of Ero1 and XBP1 significantly improves the cell's capability to express a protein of interest resulting in higher yields of the protein of interest.

The present invention also provides an isolated polynucleotide comprising a polynucleotide sequence encoding Ero1 or a variant thereof which substantially retains the function of Ero1; and a polynucleotide sequence encoding XBP1 or a variant thereof which substantially retains the function of XBP1.

BRIEF DESCRIPTION OF THE FIGURES

In the following drawings specific embodiments of the present invention are described by way of example only, in which:

FIG. 1a shows the amino acid sequence of the spliced form of human XBP1 (hXBP1s) (SEQ ID NO:1). The * denotes a stop codon.

FIG. 1*b* shows the nucleic acid sequence of the spliced form of human XBP1 (hXBP1s) (SEQ ID NO:2).

FIG. 2*a* shows the amino acid sequence of human Ero1α (hEro1α) (SEQ ID NO:3).

FIG. 2*b* shows the nucleic acid sequence of human Ero1α (hEro1α) (SEQ ID NO:4).

FIG. 14 shows the glycosylation profiles of antibodies 42, 61 and 164 expressed in CHOS and CHOSXE.

DETAILED DESCRIPTION OF THE INVENTION

Figure 3A:
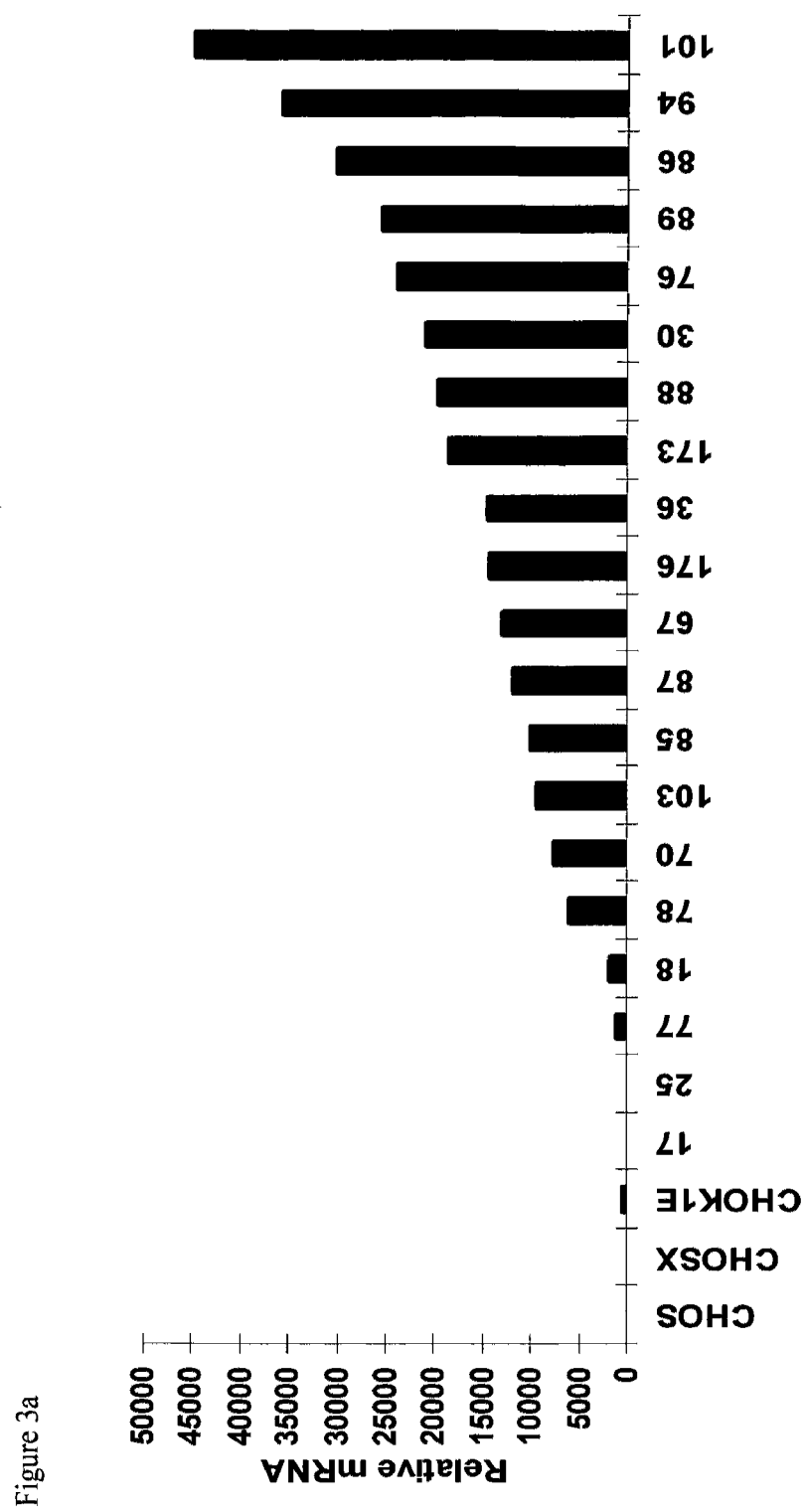
FIG. 3*a* shows hEro1α mRNA expression and FIG. 3*b* shows and hXBPs mRNA expression in CHOSXE cell clones (17, 25, 77, 18, 78, 70, 103, 85, 87, 67, 176, 36, 173, 88, 30, 76, 89, 86, 94 and 101), CHOSX and CHOK1E relative to CHOS after a first picking step of CHOSXE cell clones.

The present invention provides a recombinant host cell which has improved capacity to produce a protein of interest due to modification of the cell to increase Ero1 and XBP1 expression. The present inventors have found that an increase of Ero1 and XBP1 in a host cell significantly improves protein yield compared to an unmodified cell. Preferably the cell according to the present invention has a specific productivity of a protein of interest of 80% or more, 85% or more, 90% or more, 100% or more, 150% or more, 200% or more, 300% or more, 400% or more, 500% or more, 600% or more, 700% or more or 800% or more relative to control cells which have not been modified to increase Ero1 and XBP1. More preferably the cell according to the present invention has a specific productivity of a protein of interest of from 100% to 1000%, more preferably 200% to 1000%, still more preferably 500% to 1000% relative to control cells which have not been modified to increase Ero1 and XBP1.

Moreover, the present inventors have found that the cell according to the present invention has improved protein yield compared to a cell over expressing either Ero1 or XBP1 with the protein of interest.

In one embodiment the cell according to the present invention has a specific productivity of a protein of interest greater than the combined cellular productivity of a protein of interest from a cell modified to increase the expression of Ero1 but not XBP1 and a cell modified to increase XBP1 but not Ero1. Preferably the cell according to the present invention has a specific productivity of a protein of interest of 5% or more, 6% or more, 10% or more, 20% or more, 30% or more, 40% or more, 50% or more, 60% or more, 70% or more 80% or more, 90% or more, 100% or more, 110% or more, 120% or more, 130% or more, 140% or more, 150% or more, more preferably 5% to 150%, 6% to 130%, 10% to 130% or 50% to 130% relative to the combined cellular productivity of a protein of interest from a cell modified to increase the expression of Ero1 but not XBP1 and a cell modified to increase XBP1 but not Ero1.

Preferably the cell according to the present invention has a specific productivity of a protein of interest of 2 or more $\mu g/1\times10^6$ cells/day, preferably 3 or more $\mu g/1\times10^6$ cells/day, more preferably more than 3 $\mu g/1\times10^6$ cells/day, still more preferably 3.2 or more $\mu g/1\times10^6$ cells/day, more preferably 3.2 to 6.5 $\mu g/1\times10^6$ cells/day.

The skilled person would easily be able to test a candidate cell clone to see if it has the desired yield of a protein of interest using methods well known in the art, such as ELISA.

In a further embodiment the co-expression of both Ero1 and XBP1 provides improved yield of correctly folded proteins from the cell relative to unmodified cells. The skilled person would easily be able to test secreted protein to see if the protein is correctly folded using methods well known in the art, such as protein G HPLC, circular dichroism, NMR and X-Ray crystallography.

Without wishing to be bound by theory it is believed that the improved protein expression is due to the increased capacity of the cell to fold proteins. Specifically, increase of Ero1 expression increases the cell's capacity to form disulphide bonds in protein in the ER. In addition, the increase of XBP1 expression causes up-regulation of ER chaperone protein expression and may enlarge the size of the ER. The cell provided by the present invention may also provide an increased yield of protein relative to unmodified cells due to the increased capacity of the cell to fold all proteins expressed by the cell, which thereby increases all cellular pathways including transcription, translation, protein folding and secretary pathways. Further, due to the increase of Ero1 and XBP1 increasing the cell's capacity to process newly translated proteins, any feedback control of mRNA transcription and/or protein translation may cause an increase in protein transcription and/or translation.

In a further embodiment the co-expression of both Ero1 and XBP1 in the cell of the invention provides improved cell growth and/or stability and/or reproduction relative to unmodified cells. Preferably the cells provided by the present invention have increased cell density after the same period of culture of 30% or more, 50% or more, 60% or more, 70% or more, 80% or more, 90% or more, 100% or more, 130% or more, 150% or more, 170% or more, or 190% or more compared to the cell density of a culture of control cells which have not been modified to up-increase Ero1 and XBP1.

The skilled person would easily be able to select cells having improved cell growth and/or stability and/or reproduction by, for example, measuring the cell density and/or cell viability of a cell culture after a fixed culture period. Suitable methods known the art include the CEDEX (Innovatis) automated cell counting system based on the well-established Trypan Blue exclusion method for determining cell viability. Sample handling, staining, cell counting and graphical analysis of the results are performed automatically by the CEDEX system.

Without wishing to be bound by theory it is believed that the improved cell growth and/or stability are due to the increased capacity of the cell to process all proteins which require post-translational modifications in the ER, which thereby increases cellular pathways. Accordingly, the production of correctly folded proteins necessary for the cell's growth and reproduction may be increased thereby improving the cellular pathways regulating growth and/or stability and/or reproduction.

These findings are unexpected, particularly because XBP1 and Ero1 are not linked in a UPR pathway. The UPR is extremely complex and involves numerous different pathways. Whilst co-expression of either XBP1 or Ero1 with additional components or modulators of the same UPR pathway may be expected to improve protein expression, it is surprising that co-expression of two unconnected proteins would provide a significantly improved protein expression system.

The present invention will now be described in more detail.

The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc unless the context indicates otherwise.

As used herein, the term "comprising" in context of the present specification should be interpreted as "including".

In one aspect of the present invention there is a provided a recombinant host cell modified to increase/up-regulate/over-express the expression levels of Ero1 and XBP1 relative to the expression levels of Ero1 and XBP1 in an unmodified cell.

The unmodified cell or control cell in the context of the present invention means a cell of the same type as the host cell wherein the cell has not been modified to increase/up-regulate/over-express the expression levels of Ero1 and XBP1, for example the unmodified cell may be derived from a population of host cells before modification to increase/up-regulate/over-express the expression levels of Ero1 and XBP1.

In one embodiment the cell comprises an exogenous recombinant polynucleotide sequence encoding Ero1 or a variant thereof which substantially retains the function of Ero1; and an exogenous recombinant polynucleotide encoding XBP1 or a variant thereof which substantially retains the function of XBP1. In this embodiment the cell may comprise a polynucleotide encoding both Ero1 and XBP1 and/or the cell may comprise separate polynucleotides encoding Ero1 and XBP1.

As used herein, "the polynucleotide", "the polynucleotide encoding Ero1", "the polynucleotide encoding XBP1" and "the polynucleotide encoding Ero1 and XBP1" are intended to refer to all aspects and embodiments of the present invention wherein Ero1 and XBP1 may be encoded by the same and/or separate polynucleotides, unless stated otherwise.

Accordingly, the cell according to the present invention may comprise an exogenous Ero1 and XBP1 polynucleotide comprising both a polynucleotide sequence encoding Ero1 and a polynucleotide sequence encoding XBP1. The cell according to the present invention may also comprise such a polynucleotide in the form of an expression cassette or a vector.

Alternatively or additionally, the cell according to the present invention comprises an exogenous Ero1 polynucleotide comprising the polynucleotide sequence encoding Ero1 and a separate exogenous XBP1 polynucleotide comprising the polynucleotide sequence encoding XBP1. Accordingly, the cell according to the present invention may comprise an Ero1 expression cassette or vector comprising the Ero1 polynucleotide and a separate XBP1 expression cassette or vector comprising the XBP1 polynucleotide.

In a further embodiment the increased Ero1 and XBP1 expression is from modulation of endogenous polynucleotides encoding Ero1 and XBP1 in the cell according to the present invention. In this embodiment the cell is modified to increase transcription and translation of the endogenous genes of Ero1 and XBP1.

The cell according to the present invention may further comprise a polynucleotide sequence encoding a protein of interest. The polynucleotide sequence encoding the protein of interest may be exogenous or endogenous. The polynucleotide sequence encoding the protein of interest may be integrated into the host's chromosome or may be non-integrated in an episome.

In the embodiment wherein the polynucleotide sequence encoding the protein of interest is exogenous and the cell comprises one or more exogenous polynucleotides encoding Ero1 and XBP1, the polynucleotide sequence encoding the protein of interest may be part of one or more of the Ero1 and/or XBP1 encoding exogenous polynucleotides. Accordingly, the polynucleotide sequence encoding a protein of interest may be in the same polynucleotide sequence as both XBP1 and Ero1 e.g. the same expression cassette or vector. Alternatively or additionally the polynucleotide sequence encoding a protein of interest may be in the same polynucleotide sequence as either the separate Ero1 polynucleotide sequence and/or the separate XBP1 polynucleotide sequence e.g. the same expression cassette or vector. Alternatively or additionally, the cell may further comprise a separate polynucleotide, an expression cassette or a vector comprising the polynucleotide sequence encoding the protein of interest.

Suitable cells for employing in the invention include eukaryotic cells, for example plant cells, insect cells, yeast cells, animal cells such as mammalian cells, in particular CHO cells, myeloma cells, viro cells, MRC5 Cells, HEK cells, NSO cells, SP2 cells and the like.

CHO cells have been found to be particularly useful for mammalian expression because the proteins expressed in CHO cells have glycoforms that are generally compatible and bioactive in humans. Accordingly, in one aspect the invention employs a mammalian cell such as a CHO cell, for example a CHOS cell (Invitrogen Cat. No. 11619-012, Deaven, L. L. et al, 1973, Chromasoma 41, 129, D'Anna, J. A. et al, 1996, Methods in Cell Science 18, 115, D'Anna, J. A. et al, 1997, Radiation Research 148, 260) or CHOK1 cell (Puck, T. et al. 1967, Genetics of Somatic Mammalian Cells IV Properties of Chinese Hamster Cell Mutants With Respect To The Requirement For Proline; Genetics; 55; 513-524; March 1967), or a derivative therefrom.

In one embodiment the cell provided by the present invention is the modified CHOS cell strain Depositor Deposit Name: CHOSXE (Depositor Identification in Full: CHOS.Xbp1.Ero1a), which was deposited on 10 Feb. 2010 by UCB Celltech, the UK branch of UCB Pharma S.A., at the European Collection of Cell Cultures (ECACC), HPA, United Kingdom, under HPA Culture Collections Reference Number: Q8515 and Accession number: 10021001 in accordance with The Budapest Treaty.

As used herein, "Ero1" means a polypeptide having the activity of facilitating disulphide bond formation by oxidizing PDI. Ero1 polypeptide is formerly known as Sec81.

Any suitable form of Ero1 from any suitable source may be used in the present invention including Ero1α and Ero1β. Typically human Ero1-Lα and/or Ero1-Lβ may be used in the present invention.

In one embodiment, the polynucleotide encoding Ero1 used in the present invention encodes a variant polypeptide of the endogenous form of Ero1 which substantially retains the activity of oxidizing PDI.

A variant polypeptide in the context of the present specification is intended to refer to a sequence that has one or more amino acid substitutions, deletions or insertions compared to the endogenous polypeptide but retains all or substantially all of the function such as 80% or more, in particular 90% or more, for example 95% or more or 100% of the activity of the endogenous polypeptide.

The polynucleotide sequence encoding Ero1 used in the present invention preferably encodes an Ero1α polypeptide sequence comprising the polypeptide sequence shown in SEQ ID NO: 3. Amino acids 1 to 23 of SEQ ID NO:3 encode a signal peptide. Accordingly the polynucleotide sequence encoding Ero1 used in the present invention may or may not comprise the signal peptide and therefore may comprise amino acids 1 to 468 or amino acids 24 to 468. It will be appreciated that one or more amino acid substitutions, insertions or deletions may be made to SEQ ID NO: 3 without significantly altering the activity of Ero1. The effect of any amino acid substitutions, insertions or deletions can be readily tested by one skilled in the art by any suitable method. For example, an anti-Ero1 antibody may be used to determine Ero1 presence and the redox environment of the cell may be tested to determine Ero1 activity. Accordingly, in one embodiment, the polynucleotide sequence encoding Ero1 of the present invention encodes a polypeptide sequence having at least 60%, 70%, 80%, 90%, 95% or 98% identity or similarity to the sequence given in SEQ ID NO: 3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:
  phenylalanine, tyrosine and tryptophan (amino acids having aromatic side chains);
  lysine, arginine and histidine (amino acids having basic side chains);
  aspartate and glutamate (amino acids having acidic side chains);
  asparagine and glutamine (amino acids having amide side chains); and
  cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

It will be appreciated that any suitable polynucleotide sequence encoding an Ero1 polypeptide may be used. In one embodiment the polynucleotide sequence encoding Ero1 comprising the polynucleotide sequence shown in SEQ ID NO:4. The polynucleotide sequence shown in SEQ ID NO:4 may have one or more nucleotide substitutions, insertions or deletions without significantly altering the activity of Ero1. Accordingly, in one embodiment, the polynucleotide sequence encoding Ero1 comprises a sequence having at least 60%, 70%, 80%, 90%, 95% or 98% identity or similarity to the sequence given in SEQ ID NO: 4. In a further embodiment, the invention encompasses the use of polynucleotides that are complementary to, antisense to or hybridize under stringent conditions to the polynucleotide described herein.

The Ero1 employed in the present invention may be derived from any suitable source, for example human, mouse, hamster or yeast.

As used herein, "XBP1" means a polypeptide having transcription activation activity for one or more UPR genes including ER chaperone proteins.

Any suitable form of XBP1 from any suitable source may be used in the present invention.

Two isoforms of XBP-1 exist resulting from alternative splicing events. The XBP-1 gene is transcribed into a mRNA which encodes an unspliced version of XBP-1 and a shorter spliced mRNA is also generated which lacks exons. XBP-1 mRNA is spliced in response to ER stress, such as the accumulation of unfolded protein in the ER. It has been shown that only the spliced form of XBP-1 can efficiently activate the UPR pathway (Yoshida et al., 2001, Cell, 107, 881-891). Accordingly, the polynucleotide according to the present invention preferably encodes the spliced form of XBP1.

In one embodiment, the polynucleotide encoding XBP1 used in the present invention encodes a variant polypeptide of the endogenous form of XBP1 which substantially retains the transactivator activity of XBP1.

The polynucleotide sequence encoding XBP1 used in the present invention preferably encodes a polypeptide sequence comprising the polypeptide sequence shown in SEQ ID NO: 1. It will be appreciated that one or more amino acid substitutions, insertions or deletions may be made to SEQ ID NO: 1 without significantly altering the activity of XBP1. The effect of any amino acid substitutions, insertions or deletions can be readily tested by one skilled in the art. For example, a BODIPY staining method may be used to measure the size of the ER because XBP1 activity increases the size of the ER. The activity of choline cytidylyltransferase alpha (CCTalpha) may also be used to determine XBP1 activity because the activity of CCT alpha is increased by XBP1 over-expression.

In one embodiment, the polynucleotide sequence encoding XBP1 of the present invention encodes a polypeptide sequence having at least 60%, 70%, 80%, 90%, 95% or 98% identity or similarity to the sequence given in SEQ ID NO: 1.

It will be appreciated that any suitable polynucleotide sequence encoding an XBP1 polypeptide may be used. In one embodiment the polynucleotide sequence encoding XBP1 comprises the polynucleotide sequence shown in SEQ ID NO:2, wherein SEQ ID NO:2 is the spliced form of XBP1. The polynucleotide sequence shown in SEQ ID NO:2 may have one or more nucleotide substitutions, insertions or deletions without significantly altering the activity of XBP1. Accordingly, in one embodiment, the polynucleotide sequence encoding XBP1 comprises a sequence having at least 60%, 70%, 80%, 90%, 95% or 98% identity or similarity to the sequence given in SEQ ID NO: 2. In a further embodiment, the invention encompasses the use of polynucleotides that are complementary to, antisense to or hybridize under stringent conditions to the polynucleotide described herein.

The XBP1 employed in the present invention may be derived from any suitable source, for example human, mouse, hamster or yeast.

The cell according to the present invention may be further modified to increase the expression levels of a further component of the unfolded protein response (UPR) pathway relative to the expression levels of the further component and/or modulator of the UPR pathway in an unmodified cell. In one embodiment, the cell further comprises one or more exogenous polynucleotide sequence encoding one or more components and/or modulators of the unfolded protein response (UPR) pathway. Alternatively or additionally, the one or more up-regulated UPR pathway components and/or modulators are from modulation of one or more endogenous polynucleotides encoding the one or more UPR pathway components and/or modulators.

The presence of one or more further components and/or modulators of the UPR pathway may further improve the expression of a protein of interest in a host cell according to the present invention.

In one embodiment the modified cell according to the present invention expresses a protein of interest. "Protein of interest" in the context of the present specification is intended to refer to polypeptide for expression, usually a recombinant polypeptide. However, the protein of interest may be an endogenous protein expressed from an endogenous gene in the host cell.

As used herein, a "recombinant polypeptide" refers to a protein that is constructed or produced using recombinant DNA technology. The protein of interest may be an exogenous sequence identical to the endogenous protein or a mutated version thereof, for example with attenuated biological activity, or fragment thereof, expressed from an exogenous vector. Alternatively, the protein of interest may be a heterologous protein, not normally expressed by the host cell.

The protein of interest may be any suitable protein including therapeutic, prophylactic or diagnostic protein.

The protein of interest expressed by the cells according to the invention may, for example be an immunogenic protein, a fusion protein comprising two heterologous proteins or an antibody. Antibodies for use as the protein of interest include monoclonal, multi-valent, multi-specific, humanized, fully human or chimeric antibodies. The antibody may be a complete antibody molecule having full length heavy and light chains or a fragment thereof, e.g. VH, VL, VHH, Fab, modified Fab, Fab', F(ab')$_2$, Fv or scFv fragment.

After expression antibody fragments may be further processed, for example by conjugation to another entity or for example the antibody fragments may be PEGylated to generate a product with the required properties, for example similar to the whole antibodies, if required.

The cell, one or more polynucleotides, one or more expression cassettes and one or more vectors employed in the present invention may also comprise further polynucleotide sequences encoding one or more further proteins of interest.

The polynucleotides employed in the present invention may be incorporated into the host cell using any suitable means known in the art. Typically, each polynucleotide is incorporated as part of an expression cassette which may be integrated into the chromosome or genome of the host cell or introduced via a non-integrated expression vector. Accordingly, in one aspect the cell according to the present invention comprises an expression cassette comprising one or more polynucleotides encoding Ero1 and XBP1. In one embodiment the cell according to the present invention may comprise an expression cassette comprising both the Ero1 polynucleotide sequence and the XBP1 polynucleotide sequence. In a further embodiment, the cell according to the present invention comprises an Ero1 expression cassette comprising the Ero1 polynucleotide and a separate XBP1 expression cassette comprising the XBP1 polynucleotide sequence.

The polynucleotide sequence encoding a protein of interest may be in the same expression cassette as both XBP1 and Ero1. Alternatively or additionally the polynucleotide sequence encoding a protein of interest may be in the same expression cassette as the Ero1 polynucleotide sequence. Alternatively or additionally the polynucleotide sequence encoding a protein of interest may be in the same expression cassette as the XBP1 polynucleotide sequence. Alternatively or additionally, the cell may further comprise a separate expression cassette comprising the polynucleotide sequence encoding the protein of interest.

The expression cassette employed in the present invention typically comprises one or more protein coding sequences and one or more regulatory expression sequences. The one or more regulatory expression sequences may include a promoter. The one or more regulatory expression sequences may also include a 3' untranslated region such as a polyadenylation sequence or other termination sequences. In one embodiment, each expression cassette comprises a promoter, a protein coding sequence and a polyadenylation sequence. Suitable promoters are discussed in more detail below.

In the embodiment wherein the expression cassette comprises two or more polynucleotide sequences encoding proteins selected from Ero1, XPB1 and the protein of interest, each coding sequence is operatively linked to one or more suitable regulatory expression sequences to allow expression of each protein.

The expression cassette may further comprise one or more further UPR components and/or modulators, wherein each UPR component and/or modulator is operatively linked to one or more suitable regulatory expression sequences.

In one embodiment, the cell according to the present invention comprises a vector, such as plasmid. The vector preferably comprises one or more of the expression cassettes as defined above. In one embodiment the cell according to the present invention may comprise a vector comprising both the Ero1 polynucleotide sequence and the XBP1 polynucleotide sequence. In a further embodiment, the cell according to the present invention comprises an Ero1 vector comprising the Ero1 polynucleotide and a separate XBP1 vector comprising the XBP1 polynucleotide sequence.

The polynucleotide sequence encoding a protein of interest may be in the same vector as both XBP1 and Ero1. Alternatively or additionally the polynucleotide sequence encoding a protein of interest may be in the same vector as the Ero1 polynucleotide sequence. Alternatively or additionally the polynucleotide sequence encoding a protein of interest may be in the same vector as the XBP1 polynucleotide sequence. Alternatively or additionally, the cell may further comprise a separate vector comprising the polynucleotide sequence encoding the protein of interest.

In the embodiments of the present invention wherein a polynucleotide sequence comprises two or more encoding sequences for two or more proteins selected from Ero1, XBP1, one or more further UPR components and/or modulators and one or more proteins of interest, the polynucleotide sequence may comprise one or more internal ribosome entry site (IRES) sequences which allows translation initiation in the middle of mRNA. An IRES sequence may be positioned between encoding polynucleotide sequences to allow separate translation of the mRNA to produce the encoded polypeptide sequences.

The vector for use in the present invention may be produced by inserting an expression cassette as defined above into a suitable vector. Alternatively, the regulatory expression sequences for directing expression of each polynucleotide sequence encoding a protein may be contained in the vector and thus only the encoding region of the one or more polynucleotides may be required to complete the vector.

The vectors employed in the present invention are capable of accommodating one or more polynucleotide sequences encoding proteins selected from Ero1, XBP1, the protein of interest and optionally one or more further UPR components and/or modulators.

Examples of vectors which may be employed to transfect the host cell with a polynucleotide according to the invention include:
- a plasmid, such as an expression vector, and/or
- a viral vector such as bacterial phage, lentiviral, episomal eg BPV, vaccina, SV40.

An example of a suitable starting vector is pcDNA3 (Invitrogen).

The promoters employed in the present invention can be linked to the relevant polynucleotide directly or alternatively be located in an appropriate position, for example in a vector such that when the relevant polypeptide is inserted the relevant promoter can act on the same. One promoter may be employed for all the encoded sequences but greater levels of expression are generally obtained when each polypeptide encoded has a specific promoter.

Therefore in one embodiment one, two, three or more promoters are employed.

In one embodiment one or more promoters are located in the polynucleotide employed in the invention.

In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding polynucleotide portion.

The promoters employed in the present invention may be the same or different for each polynucleotide. The promoters may be endogenous or exogenous to the host cells. Suitable promoters include CMV such as hCMV (for example suitable as a promoter when the polypeptide is an antibody), viral LTR promoters and SV40 promoter.

One or more promoters employed may be inducible promoters.

In one embodiment, the polynucleotide employed in the present invention comprises a polyadenylation signal sequence, for example, associated with each polynucleotide sequence encoding a protein selected from Ero1, XBP1 and the protein of interest as appropriate, such as at the end of (for example at the C-terminal (3 prime) end of) each encoding polynucleotide. Expression vectors, in particular, may require signal sequences that encode for a polyadenylation tail. The polyadenylation signal sequence causes a polyadenylation tail to be added at the end of the transcribed pre-mRNA that may protect the mRNA from exonucleases thereby stabilizing mRNA and may terminate transcription.

Examples of polyadenylation tails include SV40poly A, BgH polyA and synthetic polyA tail, in particular SV40 poly A.

In one embodiment the polynucleotide employed in the present invention comprises one or more introns. In one embodiment the polynucleotide sequence comprises an intron before the start codon, i.e. at the 5 prime end. In one embodiment the polynucleotide sequence comprises an intron after the stop codon, i.e. at the 3 prime end. In one embodiment the polynucleotide sequence comprises 1, 2 or 3 introns. In one embodiment the polynucleotide sequence comprises an intron before the start codon and after the stop codon. The intron may be derived from any gene, particularly a gene from which the encoded sequence is derived.

In one or more embodiments the polynucleotide employed in the present invention comprises a Kozak sequence associated with each polynucleotide sequence encoding a protein selected from Ero1, XBP1 and the protein of interest as appropriate. Whilst not wishing to be bound by theory it is thought that the Kozak sequence is an optimal ribosome binding site.

Embodiments of the invention described herein with reference to the polynucleotide apply equally to alternative embodiments of the invention, for example vectors, expression cassettes and/or host cells comprising the components employed therein, as far as the relevant aspect can be applied to same.

The present invention also provides a method comprising modifying a cell to increase the capability of the cell to increase the expression levels of Ero1 and XBP1 relative to the expression levels of Ero1 and XBP1 in an unmodified cell.

The increase of Ero1 and XBP1 may be performed using any suitable means known in the art. For example, the cell may be transfected with one or more polynucleotides, one or more expression cassettes and/or one or more vectors encoding:
- an exogenous polynucleotide sequence encoding Ero1 or a variant thereof which substantially retains the function of Ero1; and
- an exogenous polynucleotide sequence encoding XBP1 or a variant thereof which substantially retains the function of XBP1.

In this embodiment the one or more polynucleotides, one or more expression cassettes and/or one or more vectors are as described above. Accordingly, the method according to the present invention may employ the polynucleotide according to the present invention wherein the polynucleotide comprises a polynucleotide sequence comprising Ero1 and a polynucleotide sequence comprising XBP1. Additionally or alternatively, the method according to the present invention employs separate polynucleotides encoding Ero1 and XBP1, as described above.

In an additional or alternative embodiment, Ero1 and XBP1 expression is increased from modulation of endogenous polynucleotides encoding Ero1 and XBP1 in the cell. In this embodiment the cell is modified to increase transcription and translation of the endogenous genes of Ero1 and XBP1. Any suitable method to increase expression of endogenous genes may be used. For example, an agent, such as Tunicamycin or Thapsigargin, may be used to cause cell stress and thereby stimulating UPR and Ero1 and XBP1 increase. A further example is the use of an agent, such as CpG binding protein (a transcriptional activator that binds unmethylated CpG motifs), may be used to enhance the transcription of genes including Ero1 and XBP1.

The one or more polynucleotides employed in the present invention, preferably in the form of one or more expression cassettes or one or more vectors, can be incorporated into a cell in various ways. In one embodiment the one or more polynucleotides are integrated into a chromosome or the genome of the cell to allow stable expression. In a further embodiment of the invention the cell is transiently transfected using, for example a non-integrating vector.

In the embodiment wherein the Ero1 polynucleotide sequence and XBP1 polynucleotide sequence are separate, each polynucleotide sequence, preferably in the form of an expression cassette or vector, may be introduced into a cell simultaneously or sequentially.

The one or more polynucleotide sequences can be introduced into a cell using standard techniques, for example employing electroporation, or lipid based methods (lipotransfection), anionic transfection, cationic transfection such as employing calcium phosphate, heat shock, magnetofection, transfection agents such as lipofectamine, dendrimers, DEAE-dextran transfection, transduction employing a virus. In one embodiment cationic transfection such as employing calcium phosphate is employed.

The method according to the present invention may also employ a selection system to facilitate selection of stable cells which have been successfully transfected with the one or more polynucleotides. The selection system typically employs co-transfection of a polynucleotide sequence encoding a selection marker. In one embodiment, each polynucleotide transfected into the cell further comprises a polynucleotide sequence encoding one or more selection markers. Accordingly, the transfection of the one or more polynucleotides of the present invention and the one or more polynucleotides encoding the marker occurs together and the selection system can be employed to select those cells which produce the desired proteins.

Cells able to express the one or more markers are able to survive/grow/multiply under certain artificially imposed conditions, for example the addition of a toxin or antibiotic, because of the properties endowed by the polypeptide/gene or polypeptide component of the selection system incorporated therein (e.g. antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Typically the selection system may be based on including in the vector one or more genes that provides resistance to a known antibiotic, for example a kanamycin or ampicillin resistance gene. Cells that grow in the presence of a relevant antibiotic can be selected as they express both the gene that gives resistance to the antibiotic and the desired protein. Other suitable selection systems include the use of geneticin, also known as G418, which is a toxin that can be neutralized by the product of a neomycin resistant gene; the use of the enzyme dihydrofolate reductase (DHFR), which is essential for the de novo synthesis of glycine, purine and thymidine, optionally in combination with an inhibitor of DHFR namely, methotrexate; and the use of glutamine synthetase (GS), which catalyses the formation of glutamine from glutamate and ammonia, optionally in combination with an inhibitor of GS, such as methionine sulphoximine (MSX). The Zeocin™ selection system may also be employed in the present invention. Zeocin™ is an antibiotic from *Streptomyces* and the selection system employs the use of a Zeocin™ resistant protein.

In one embodiment, the method according to the present invention further comprises the step of culturing the transfected cell in a medium to thereby express increased levels of Ero1 polypeptide and XBP1 polypeptide and optionally any selection marker.

In this embodiment the method according to the present invention may further comprise the following steps:

a. selecting one or more modified cell clones;
b. measuring the quantity of Ero1 mRNA and/or protein in the selected one or more cell clones; and
c. measuring the quantity of XBP1 mRNA and/or protein in the selected one or more clones.

Steps b and c may be carried out simultaneously or sequentially in any order. The skilled person would know from their common general knowledge suitable method for measuring the mRNA and/or protein levels of Ero1 or XBP1 in modified cell clones. Techniques for measuring the increase of Ero1 and XBP1 expression include ELISA for protein quantification and Taqman quantitative PCR analysis and Northern Blot analysis for mRNA quantification.

The method preferably further comprises the steps of:

d. comparing the quantity of Ero1 mRNA and/or protein and XBP1 mRNA and/or protein to the quantity of Ero1 mRNA and/or protein and XBP1 mRNA and/or protein in an unmodified cell clone; and
e. selecting one or more modified cell clones having a higher quantity of Ero1 mRNA and/or protein and XBP1 mRNA and/or protein compared to the unmodified cell clone.

In step d the quantity of Ero1 mRNA and/or protein and XBP1 mRNA and/or protein is compared to the quantity of Ero1 mRNA and/or protein and XBP1 mRNA and/or protein in an unmodified cell clone. Alternatively the quantity of Ero1 mRNA and/or protein and XBP1 mRNA and/or protein may be compared to the quantity of Ero1 mRNA and/or protein and XBP1 mRNA and/or protein in one or more other modified cell clones. In this embodiment, step e may comprise selection of the modified cell clones showing a higher quantity of Ero1 mRNA and/or protein and XBP1 mRNA and/or protein compared to other modified cell clones.

In step e, any suitable number of modified cell clones may be selected which have higher quantity of Ero1 mRNA and/or protein and XBP1 mRNA and/or protein compared to the unmodified cell clone. Typically one or more cell clones having the highest quantity of Ero1 mRNA and/or protein and XBP1 mRNA and/or protein are selected. The one or more cell clones which are selected in step e may then be selected for further growth and use for expressing a protein of interest. The method may comprise repeating steps b, c, d and e one or more times.

The skilled person would easily be able to identity modified cell clones having a higher quantity of Ero1 mRNA and XBP1 mRNA compared to the unmodified cell clone, such as a CHOS cell. Examples of suitable relative quantity of Ero1 mRNA and XBP1 mRNA compared to a CHOS cell which has no detectable Ero1 mRNA and XBP1 mRNA (which is counted as 1 for the purpose of calculating relative amount), may be for Ero1 mRNA: 5000 or more fold increase, 5000 to 500000 fold increase, 10000 to 400000 fold increase, 30000 to 400000 fold increase, 100000 to 400000 fold increase; and for XBP1 mRNA: 150 or more fold increase, 150 to 150000 fold increase, 300 to 110000 fold increase, 5000 to 110000 fold increase.

The present invention also provides one or more modified cell clones as produced by the method described above. The present inventors have found that the modified cell clones produced by the above method are capable of expressing a protein of interest at a higher yield compared to an unmodified cell clone.

In one embodiment the method further comprises transfecting the host cell with a polynucleotide sequence encoding a protein of interest and expressing the protein of interest. The method may also include a further step of measuring the quantity of expression of the protein of interest and selecting one or more cell clones having high expression levels of the protein of interest. Accordingly, the present invention also provides a method of producing a recombinant protein of interest comprising expressing the recombinant protein of interest in a modified host cell in which the expression levels of XBP1 and Ero1 are increased. Suitable proteins of interest are described above.

In the embodiment wherein the cell is also transfected with a polynucleotide sequence encoding a protein of interest which is a separate polynucleotide to the one or more Ero1 and XBP1 polynucleotides, the polynucleotide sequence encoding a protein of interest may be introduced into the host cell simultaneously with the one or more Ero1 and XBP1 polynucleotides, wherein the Ero1 and XBP1 polynucleotide sequences may be in the same or separate polynucleotides. Alternatively, the polynucleotide sequence encoding a protein of interest may be introduced into the host cell before or after the one or more Ero1 and XBP1 polynucleotides are introduced into the host cell. In the embodiment wherein the Ero1 and XBP1 polynucleotide sequences are separate polynucleotides the polynucleotide sequence encoding a protein of interest may be introduced into the host cell before or after one or both of the Ero1 and XBP1 polynucleotides.

In a preferred embodiment the polynucleotide sequence encoding a protein of interest is introduced into the host cell after the one or more Ero1 and XBP1 polynucleotides have been introduced into the host cell and, more preferably the polynucleotide sequence encoding a protein of interest is introduced into the host cell after the modified cells have been selected which show increased Ero1 and XBP1 expression.

An inducible expression system may be used in the present invention to express the Ero1 protein and/or the XBP1 protein and/or the protein of interest. Suitable inducible expression systems are well known in the art.

In one embodiment wherein the cell comprises a polynucleotide sequence encoding a further component and/or modulator of the UPR pathway, the method may further comprise a step of expressing the further component and/or modulator of the UPR pathway.

Any suitable medium may be used to culture the transfected cell. The medium may be adapted for a specific selection system, for example the medium may comprise an antibiotic, to allow only those cells which have been successfully transfected to grow in the medium. The method according to the present invention may also comprise a step of selecting those cells in the medium which have been successfully transfected, such as by selecting cells which are able to grow in the medium.

The cells obtained from the medium may be subjected to further screening and/or purification as required. In the embodiment wherein the cell comprises a polynucleotide sequence encoding a protein of interest and the protein of interest is expressed, the method may further comprise one or more steps to extract and purify the protein of interest as required.

One or more method steps described herein may be performed in combination in a suitable container such as a bioreactor.

The present invention also extends to cell cultures that are transfected or transduced with one or more polynucleotides, as described herein, preferably in the form of one or more expression cassettes or one or more vectors, as described above.

The present inventors have demonstrated that the co-expression of both Ero1 and XBP1 in a cell provides improved means for expressing a protein of interest.

As discussed above, with respect to the cell according to the present invention, in a preferred embodiment the method according to the present invention increases the yield of expressed protein of interest from the cell compared to the yield of expressed protein of interest from an unmodified cell which has not been modified to increase either Ero1 or XBP1, more preferably compared to the yield of expressed protein of interest from a cell which has been modified to increase either Ero1 or XBP1 and still more preferably compared to the combined yield of expressed protein of interest from a cell modified to increase the expression of Ero1 but not XBP1 and a cell modified to increase XBP1 but not Ero1.

Further, as discussed previously, the method according to the present invention preferably provides a cell having increased cell growth and/or stability and/or reproduction after the same period of culture relative to unmodified cells which have not been modified to increase Ero1 and XBP1.

The present invention also provides an isolated polynucleotide comprising a polynucleotide sequence encoding Ero1 or a variant thereof which substantially retains the function of Ero1; and a polynucleotide sequence encoding XBP1 or a variant thereof which substantially retains the function of XBP1. Suitable polynucleotide sequences including preferred sequences are described above with respect to the cell according to the present invention, wherein both Ero1 and XBP1 are part of the same polynucleotide sequence. In one embodiment, the polynucleotide according to the present invention may further comprise a polynucleotide sequence encoding a protein of interest and/or a further component of the UPR pathway, as described previously.

The present invention also provides an expression cassette and a vector comprising the polynucleotide according to the present invention.

The invention also extends to an expression system comprising a recombinant polynucleotide sequence encoding Ero1 or a variant thereof which substantially retains the function of Ero1; a recombinant polynucleotide sequence encoding XBP1 or a variant thereof which substantially retains the function of XBP1; and a suitable medium.

The expression system may comprise a polynucleotide comprising both Ero1 and XBP1 or may comprise separate polynucleotides comprising Ero1 and XBP1. The one or more polynucleotides are preferably comprised within one or more expression cassettes and/or one or more vectors as described previously. The expression system may comprise a cell suitable for transfecting with the one or more polynucleotide. Thus the invention provides a composition comprising a polynucleotide according to the invention and a cell complementary thereto, for example in admixture and/or wherein the relevant polynucleotide is located within the cell. In one embodiment the expression system comprises a cell comprising the one or more polynucleotides as defined above.

The expression system may further comprise one or more polynucleotides encoding different proteins of interest.

The invention also extends to use of a recombinant polynucleotide sequence encoding Ero1 and a recombinant polynucleotide sequence encoding XBP1 for expressing a protein of interest.

In a further aspect the invention provides use of a recombinant polynucleotide sequence encoding Ero1 and a recombinant polynucleotide sequence encoding XBP1 in one or more expression cassettes, one or more vectors or one or more cells as described above for expressing a protein of interest.

The present invention also provides a polynucleotide as defined above, an expression cassette as defined above, a vector as defined above, a cell as defined above or an expression system as defined above for use as a medicament.

The present invention also encompasses a pharmaceutical composition comprising a polynucleotide as defined above, an expression cassette as defined above, a vector as defined above, a cell as defined above or an expression system as defined above.

The present invention also encompasses a composition comprising Ero1 protein and XBP1 protein for use as a medicament. The present invention also encompasses a pharmaceutical composition comprising Ero1 protein and XBP1 protein.

Suitable pharmaceutically acceptable carriers including solvents, solubilizers, fillers, stabilizers and the like are well known in the art. The pharmaceutical composition may be formulated for any intended route of administration including but not limited to parental, intravenous, oral, inhalation, topical and systemic administration. In one embodiment the one or more expression cassettes or one or more vectors according to the present invention are suitable for gene delivery for being introduced into a patient. In this embodiment the vector is preferably a viral vector. The one or more expression cassettes or one or more vectors may be encapsulated in a liposome for gene delivery. Various other methods of introducing genes into a patient are well known in the art.

The over-expression of both Ero1 and XBP1 or a composition comprising the combination of both Ero1 and XBP1 may be used to treat protein conformational diseases or disorders. Accordingly, the present invention also provides the use of a polynucleotide as defined above, an expression cassette as defined above, a vector as defined above, a cell as defined above, an expression system as defined above or a pharmaceutical composition as defined above for manufacture of a medicament for the treatment of a protein conformational disease or disorder. The increase of Ero1 and XBP1 may be used to treat conditions wherein Ero1 and/or XBP1 expression or activity is reduced. Typical protein conformational diseases which may be treated include, but are not limited to cystic fibrosis, α1-antitrypsin deficiency and autoimmune diseases.

In a further embodiment, wherein a polynucleotide sequence encoding a protein of interest is employed in the present invention, the protein of interest may be a therapeutic or prophylactic protein suitable for the treatment of a human or non-human animal in need thereof.

One or more embodiments of the invention described herein may be combined unless they are technically incompatible.

Specific embodiments of the invention are described herein comprising certain entities. The invention also extends to separate embodiments that consist or consist essentially of said elements.

The invention will now be illustrated by reference to the following examples.

EXAMPLES

DNA Manipulations and General Methods

CHOS cells (Invitrogen) and CHOK1 cells (ATCC) were used for transformation and routine culture growth. DNA restriction and modification enzymes were obtained from New England Biolabs.

The spliced form of human XBP1 (SEQ ID NO:2) and Human Ero1α (SEQ ID NO:4) were used.

Nucleotide sequences for Ero1α and XBP1 were chemically synthesized by Entelechon.

The pCDNA3.1(+) vectors comprising the gene of interest, were transfected into the host cells using electroporation (for CHOSX and CHOK1E cells) or lipofectamine (for CHOSXE cells).

In example 2 and 3 the mammalian expression vectors used contained both sequences encoding the heavy and light chain of an antibody. These sequences were under control of the CMV-promoter. The plasmid also included SV40E polyA tails and the glutamate synthetase selection marker.

In example 5 and 6 single gene vectors were used containing sequences encoding either the heavy or the light chain of the monoclonal antibody. No selection marker was present on the plasmid. The single gene vectors were co-transfected at a 1:1 ratio.

Lipofectamine transfections were done using Lipofectamine2000 (Invitrogen). 12.5 ul Lip2000 was diluted into 125 ul serum free Dulbecco's modified Eagle's media (SF DMEM, Invitrogen). 4 μg of the mAb expression vector DNA was diluted into 125 ul SF DMEM. DNA and Lip2000 were mixed and incubated for 20 minutes at room temperature. 500 ul SF DMEM was added to the mix which was then added to the cells to incubate at 37° C. for four hours. Subsequent to incubation, the media containing the DNA/reagent mix was replaced by 3 ml of fresh CDCHO media (Invitrogen). MAb transfections were done in duplicate.

Antibodies used in the examples were IgG antibodies of the following isotypes show in Table 1 below:

TABLE 1

| mAb | Species | Isotype | Extinction Coefficient |
| --- | --- | --- | --- |
| 146 | Mouse | IgG1 | |
| 632 | Mouse | IgG2a | |
| 497 | Human | IgG4 | |
| 240 | Human | IgG4 | |
| 42 | Mouse | IgG1 | 1.6 |
| 61 | Mouse | IgG1 | 1.62 |
| 164 | Mouse | IgG1 | 1.6 |

Levels of antibody expression were determined by ELISA unless otherwise stated.

Cell density and cell viability was measured using CEDEX (Innovatis) automated cell counting system based on the well-established Trypan Blue exclusion method for determining cell viability. Sample handling, staining, cell counting and graphical analysis of the results are performed automatically by the CEDEX system.

Example 1

Transfection of CHO Cells with Ero1α and/or XBP1

CHOSX Cell Line

The spliced form of human XBP1 [hXBP1(s)] was cloned into vector pcDNA3.1(+), this vector also contained the G418 selection system comprising the neomycin resistance gene, which generated the vector pcDNA3.hXBP1(s). CHOS cells were transfected with vector pcDNA3.hXBP1(s) and stable cell lines were selected in the presence of geneticin (1 mg/ml) to produce a CHOSX cell line expressing hXBP1(s).

CHOK1E Cell Line

Human Ero1α (hEro1α) was cloned into the pcDNA3.1(+) vector and CHOK1 cells were transfected with pcDNA3.hEro1α to produce a CHOK1E cell line expressing human Ero1α. CHOK1E cells were selected using the G418 selection system.

CHOSXE Cell Line

Human Ero1α (hEro1α) was cloned into vector pcDNA3.1 (+)(zeo) (Invitrogen) and the CHOSX cell line was then supertransfected with vector pCDNA3(zeo).hEro1α to produce the CHOSXE cell line expressing both hEro1α and hXBP1(s). Both the G418 selection system (neomycin resistance gene) and the zeocin selection system (zeocin resistance gene) were used to select successfully transfected CHOSXE cells. The cells were grown in 100-300 µg/ml of zeocin and 1 mg/ml of geneticin.

Selection of CHOSXE Clones

Pick 1:

Two weeks post transfection a first pick of 177 clones was performed of which 85 clones were positive for mRNA expression of the transgenes hEro1α and hXBP1(s) as assessed by single cell RT-PCR and PCR.

Figure 3B:

24 of the 85 positive clones were then bulked up to 6-well plates. Relative mRNA levels of hXBP1(s) and hEro1α were determined by Taqman. The results of this analysis are shown in FIGS. 3a and 3b where the relative hXBP1(s) and hEro1α mRNA levels in the CHOSXE clones are compared to CHOS cells (CHOS cells showed no expression but counted as 1 for the purpose of calculating relative mRNA amounts). Using the results shown in FIGS. 3a and 3b, 3 low hEro1α expressing clones (70, 77 and 103), 3 medium hEro1α expressing clones (76, 88 and 173) and 3 high hEro1α expressing clones (86, 94 and 101) were then selected for further analysis.

Pick 2:

A further two weeks after pick 1 was performed 72 more clones were picked of which 29 clones were positive for hXBP1(s) and hEro1α mRNA expression as assessed by RT-PCR and PCR.

Figure 4:
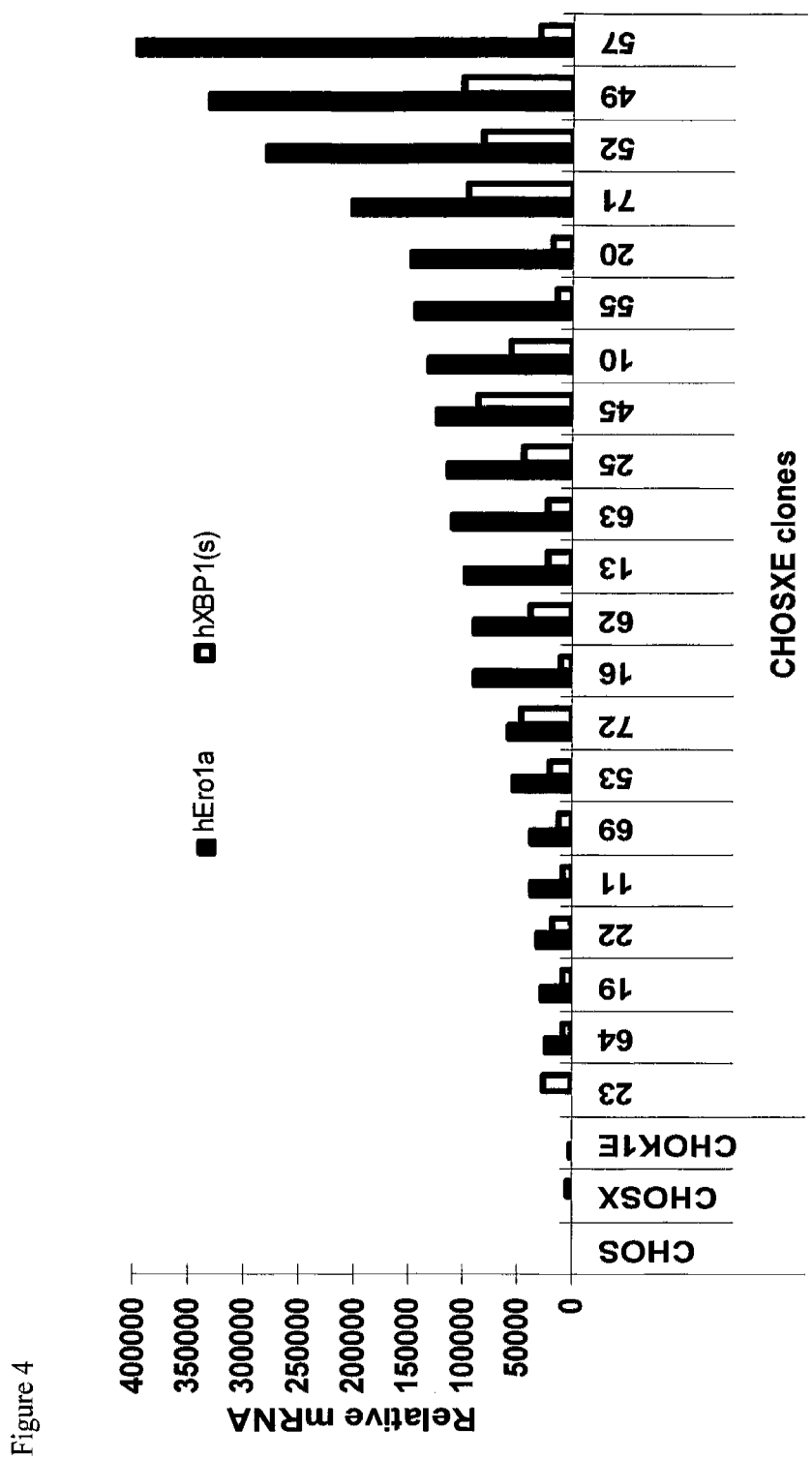
FIG. 4 shows hEro1α mRNA and hXBPs mRNA expression after pick 2 of CHOSXE cell clones in CHOSXE cell clones (23, 64, 19, 22, 11, 69, 53, 72, 16, 62, 13, 63, 25, 45, 10, 55, 20, 71, 52, 49 and 57), CHOSX and CHOK1E relative to CHOS after a second picking step of CHOSXE cell clones.

The 29 positive clones were then bulked up to 6-well plates and relative levels of hXBP1(s) and hEro1α mRNA were determined as in pick 1. The results of this analysis are shown in FIG. 4 where the mRNA levels of hXBP1(s) and hEro1α expressed in the CHOSXE clones are compared to CHOS cells (CHOS cells showed no expression but counted as 1 for the purpose of calculating relative mRNA amounts). Further mRNA analysis of clone 71 (data not shown) showed mRNA levels of 5,000 fold increase of hXBP1(s) and 110,000 fold increase of hEro1α compared to CHOS cells (CHOS cells showed no expression but counted as 1 for the purpose of calculating relative mRNA amounts). Using the results shown in FIG. 4, 3 low hEro1α expressing clones (19, 23, and 64), 3 medium hEro1α expressing clones (13, 16 and 62) and 3 high hEro1α expressing clones (49, 57 and 71) were then selected for further analysis.

Clone 71 was deposited under Depositor Deposit Name: CHOSXE (Depositor Identification in Full: CHOS.Xbp1.Ero1α), on 10 Feb. 2010 by UCB Celltech, the UK branch of UCB Pharma S.A., at the European Collection of Cell Cultures (ECACC), HPA, United Kingdom, under HPA Culture Collections Reference Number: Q8515 and Accession number: 10021001 in accordance with The Budapest Treaty.

Example 2

Transfection of CHOSXE Cells with Monoclonal Antibodies (mAbs)

The selected clones from pick 1 (70, 76, 77, 86, 88, 94, 101, 103 and 173) were transfected with DNA of mAbs 146 and 632 as described in the methods and the mAb expression was determined from culture supernatant. The 3 highest mAb expressing CHOSXE clones were selected for further analysis (clones 70, 88 and 103).

The three selected clones from pick 1 (70, 88, and 103) were then combined with the selected clones from pick 2 (13, 16, 19, 23, 49, 57, 62, 64, and 71) and transfected with DNA for mAbs 632 and 497 as described in the general methods section above. Culture supernatant sample was taken on day 4 to determine antibody concentration.

Monoclonal antibodies 632 and 497 were also transfected into CHOS and CHOSX cells using the same transfection method as described in the general methods section above.

Figure 5:
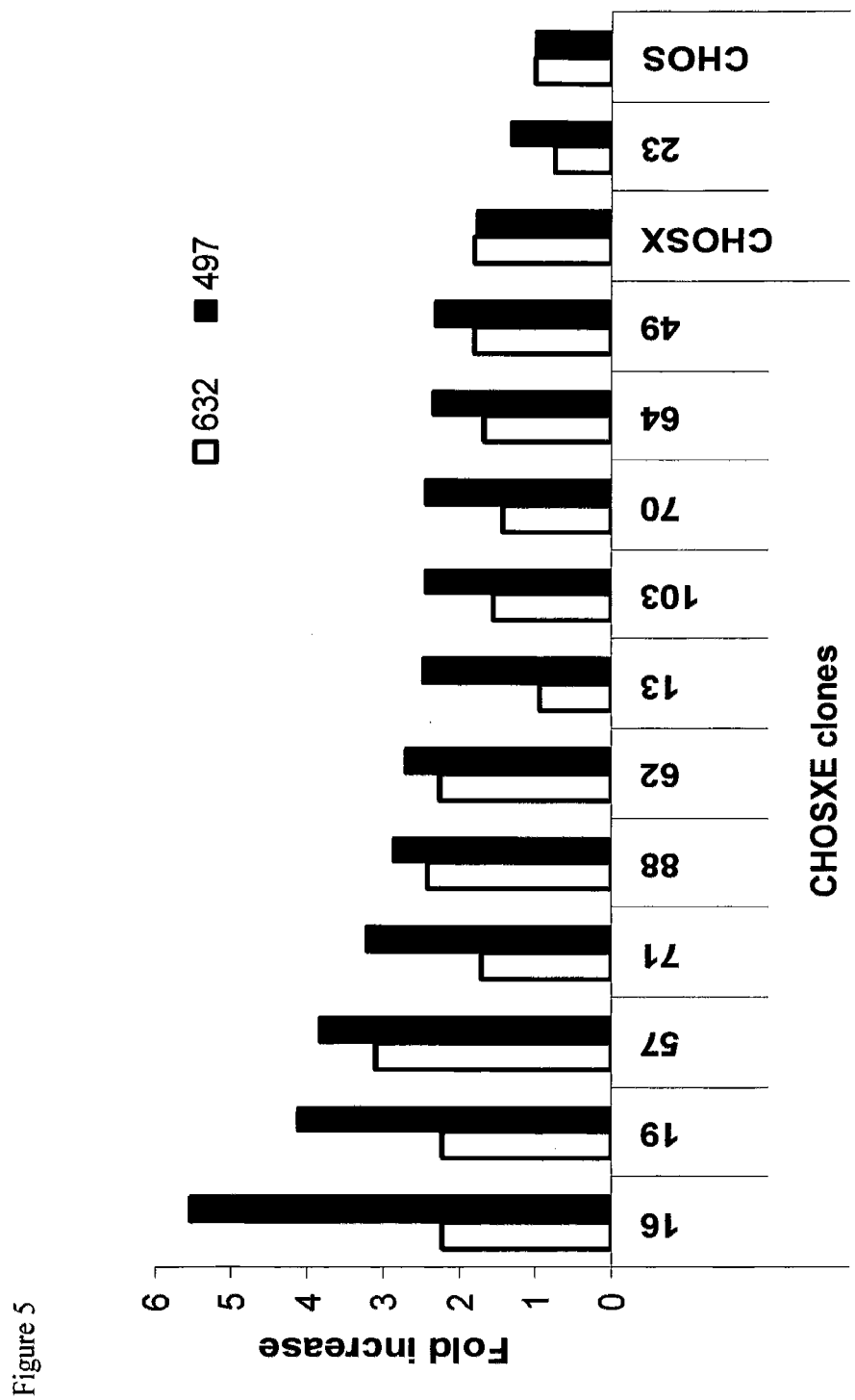
FIG. 5 shows the relative increase the expression of antibodies 632 and 497 in cell clones from a CHOS cell line transfected with hEro1α and hXBP1s (CHOSXE) and a CHOS cell line transfected with hXBP1s (CHOSX) compared to expression of antibodies 632 and 497 in a CHOS cell line.

The data for the relative increase in expression of mAbs 632 and 497 from CHOSXE and CHOSX cells compared to the expression of mAbs 632 and 497 from CHOS cells is shown in FIG. 5. The data indicates that all the CHOSXE clones, except for clone 13 and clones 23, produced increased mAb expression levels of mAb 632 compared to the CHOS clone and all the CHOSXE clones produced increased expression of mAb 497 compared to both the CHOS the CHOSX clones, except for clone 23 which expressed less mAb 497 than CHOSX.

Example 3

Transfection of CHOSXE Cells with Antibodies Ab240 and Ab146

The highest mAb expressing clones (16, 19, 57, 62, 71 and 88) produced in Example 2 were picked to perform further mAb transfections. The experiment was scaled up to T25 flask cultures and the mAb 240 and 146 were used. The transfection was performed as described above in the general methods section, but 18.75 ul Lip2000 was diluted into 1.875 ml OPTI_MEM (Invitrogen) media. 7.5 µg of antibody DNA was diluted into 1.875 ml OPTI_MEM media. 3.75 ml of OPTI_MEM media was added to the mix to add to the cells. After incubation at 37° C., 3.375 ml CD CHO media was added to the flask. This transfection method was used for CHOSXE cells, CHOSX cells, CHOK1E cells and CHOS cells.

Figure 6:
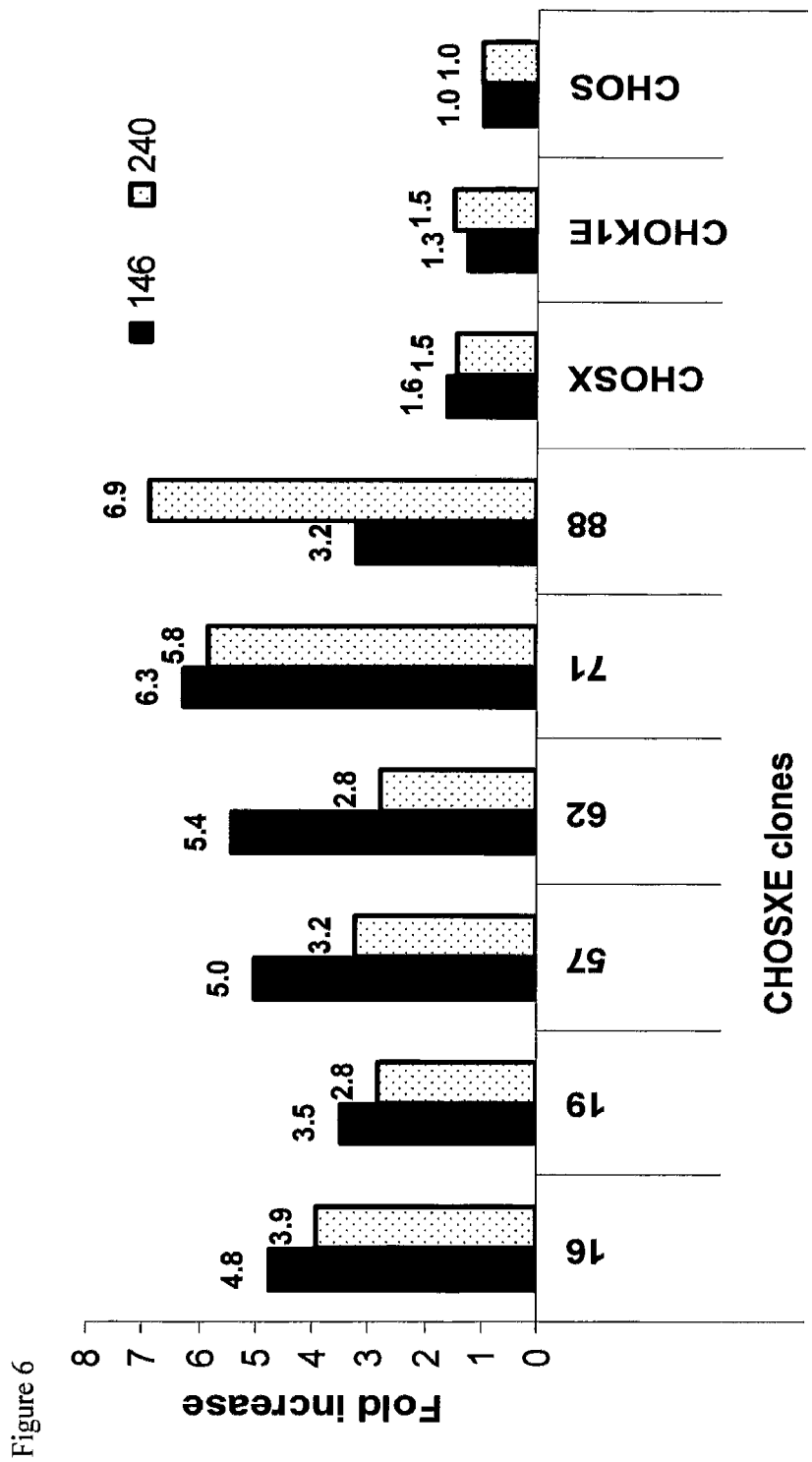
FIG. 6 shows the relative increase the expression of antibodies 146 and 240 from cell clones from a CHOS cell line transfected with hEro1α and hXBP1s (CHOSXE), a CHOS cell line transfected with hXBP1s (CHOSX) and a CHOK1 cell line transfected with hEro1α (CHOK1E) compared to expression of antibodies 146 and 240 from a CHOS cell line.

The data for the increase in expression of mAbs 240 and 146 from CHOSXE, CHOSX and CHOK1E cells compared to the expression of mAbs 240 and 146 from CHOS cells is shown in FIG. 6. In FIG. 6 clones numbered 16, 19, 57, 62, 71 and 88 are CHOSXE clones. The data indicates that all the CHOSXE clones produced increased expression of both antibodies compared to CHOS cells, CHOSX cells and CHOK1E cells.

Clone 71 was selected for further analysis and is called CHOSXE in Examples 4 to 7.

Example 4

Measurement of Cell Line Characteristics in CHOSXE, CHOSX and CHOS Cell Lines

Figure 7:
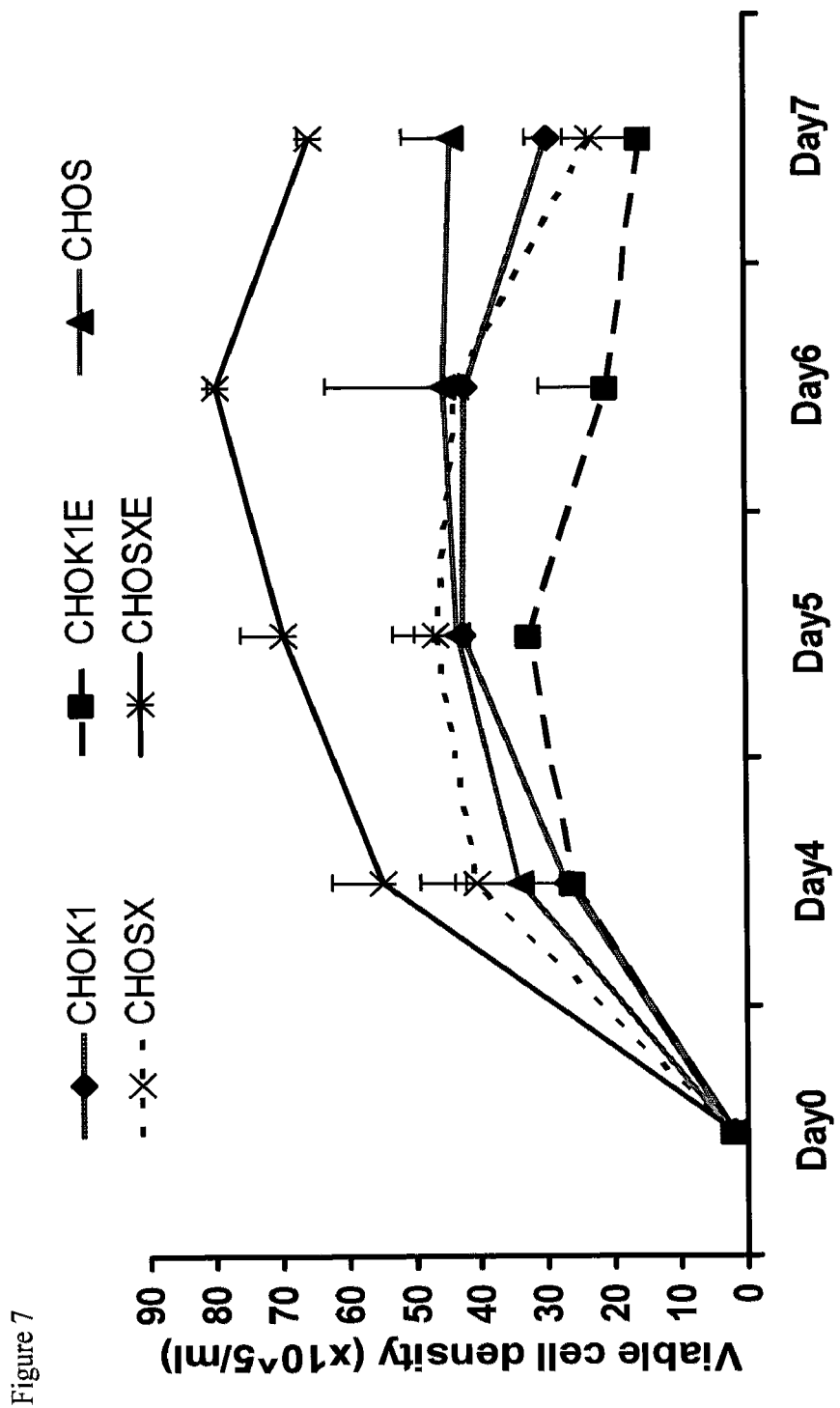
FIG. 7 shows a growth curve of cell lines CHOS, CHOSX, CHOSXE, CHOK1 and CHOK1E.

Cells from cell lines CHOSXE, CHOSX and CHOS were seeded at $2\times10^5$/ml in 50 mls CD CHO and cultured over 7 days on a shaking platform. As shown in FIG. 7, the CHOSXE cell line outperformed the CHOS, CHOSX, CHOK1 and CHOK1E cell lines by reaching higher viable cell densities.

Example 5

Electroporation of Antibodies 42, 61 and 164 into CHOSXE, CHOSX and CHOS Cell Lines 400 ug DNA of an antibody was transfected into 3 different cell lines CHOS, CHOSX and CHOSXE. Cells were shifted to 32° C. on day 1 and 3 µM NaBu added on day 4 post-transfection. The three antibodies used were labelled as mAbs 42, 61 and 164. Cell counts and cell viabilities were taken on day 1, 4, 7 and 10. Culture supernatant samples were taken on days 4, 7 and 10 to determine cells' specific productivity.

TABLE 2

% Cell viabilities and viable cell densities (VCD) on day 1 post-transfection.

| Antibody | Cell Line | VCD cells × $10^5$/ml (day 1) | % Viability (day 1) |
|---|---|---|---|
| 42 | CHOS 42 | 22.7 | 96.7 |
| 42 | CHOSX 42 | 23.85 | 96.8 |
| 42 | CHOSXE 42 | 23.05 | 97.1 |
| 61 | CHOS 61 | 23.4 | 96.8 |
| 61 | CHOSX 61 | 20.14 | 96.9 |
| 61 | CHOSXE 61 | 23.54 | 97.8 |
| 164 | CHOS 164 | 20.92 | 97.5 |
| 164 | CHOSX 164 | 22.04 | 96.5 |
| 164 | CHOSXE 164 | 23.73 | 97.5 |

It can be seen from Table 2 that CHOXE cell lines had equal or higher % viability compared to CHOS and CHOSX and that CHOSXE had comparable viable cell densities compared to CHOS and CHOSX.

Figure 8:
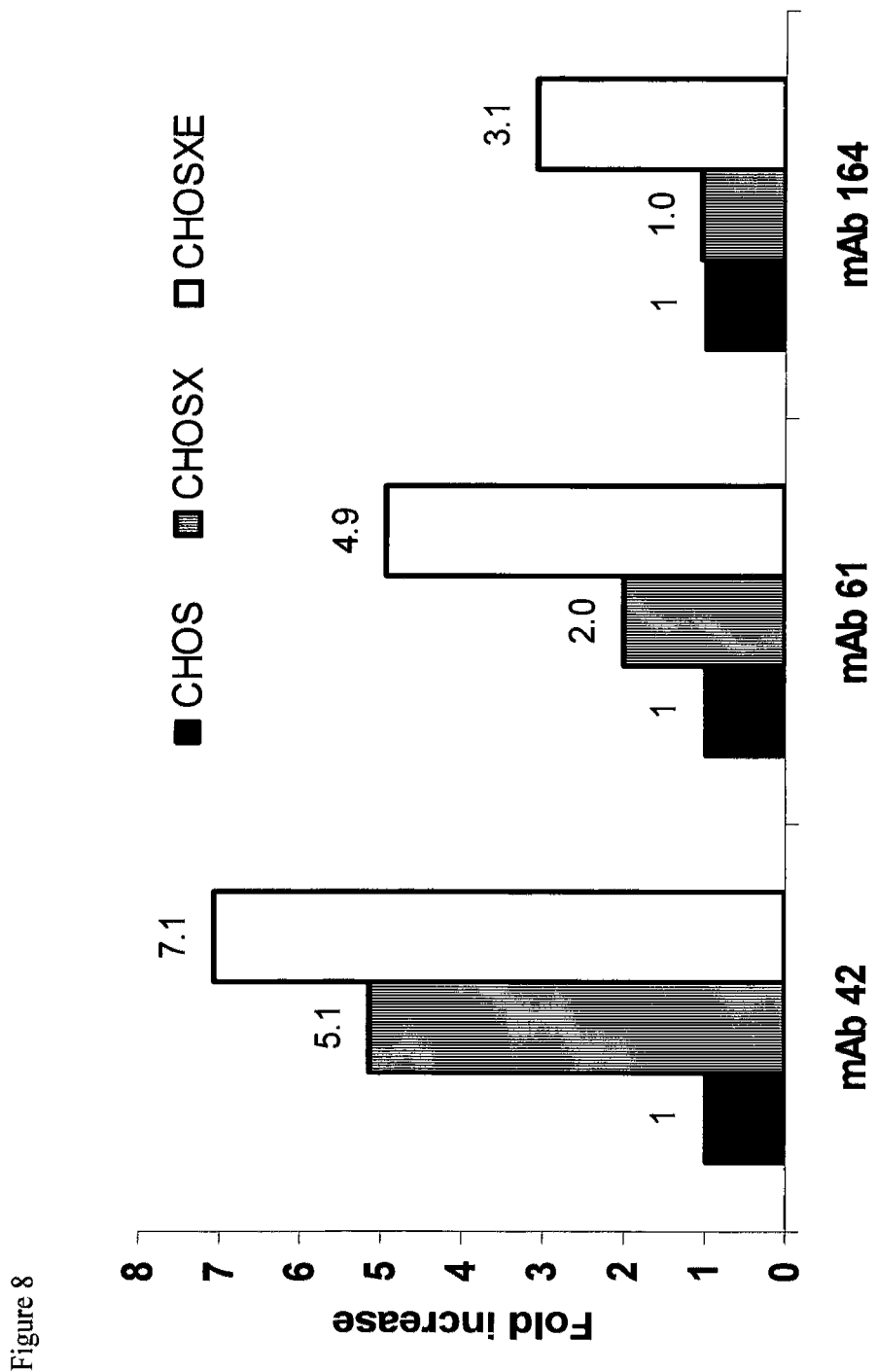
FIG. 8 shows the relative increase in expression of antibodies 42, 61 and 164 in CHOSXE and CHOSX compared to the expression of 42, 61 and 164 in CHOS cells.

FIG. 8 shows the relative increase in expression of mAbs 42, 61 and 164 from CHOSXE and CHOSX compared to the expression of mAbs 42, 61 and 164 from CHOS cells. It is clear that expression of all three antibodies was higher in CHOSXE compared to either CHOSX or CHOS.

Figure 9:
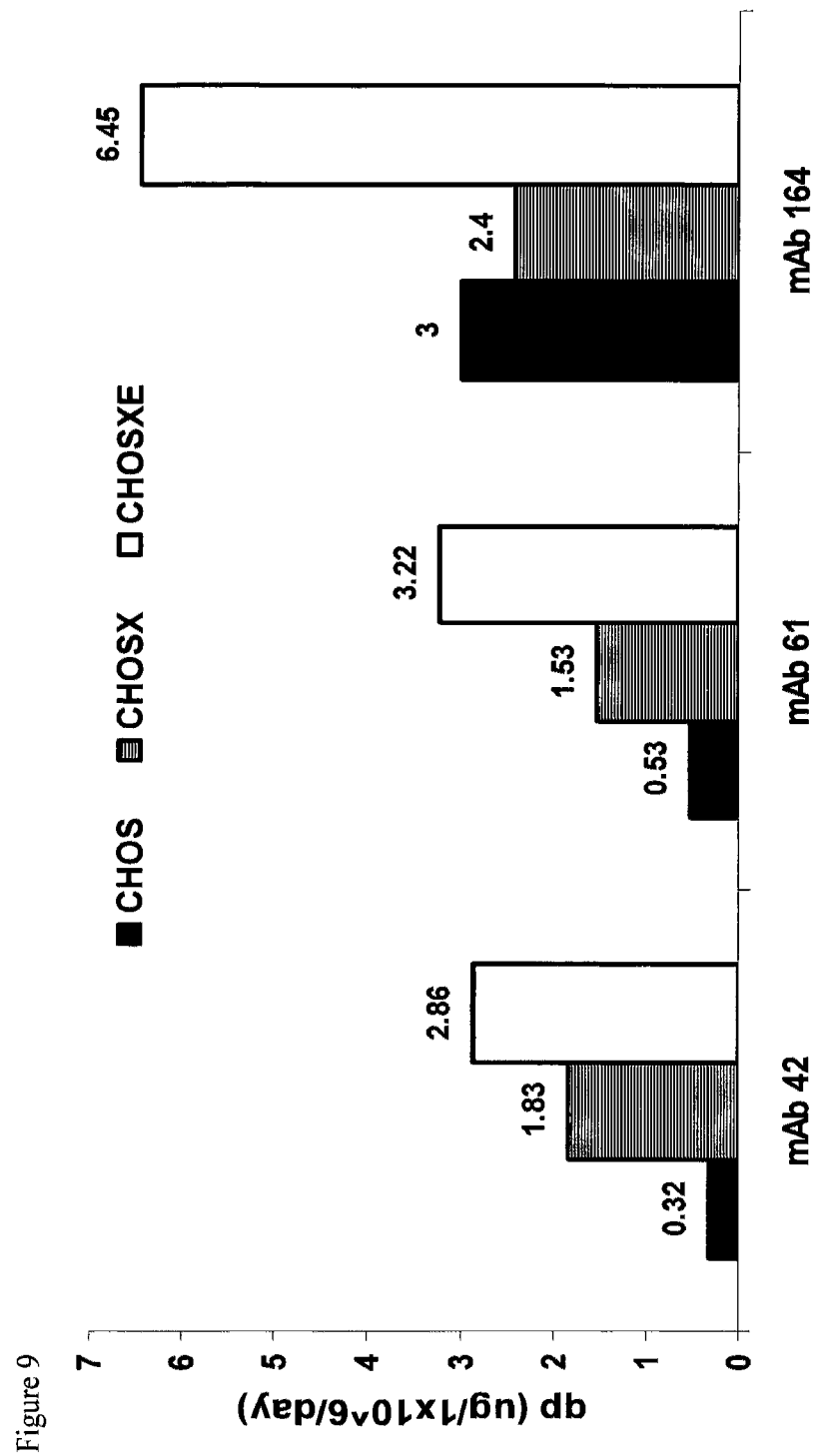
FIG. 9 shows the specific productivity of CHOS, CHOSX and CHOSXE cell lines between day 4 and day 7 for antibodies 42, 61 and 164.

The specific productivity rate (SPR) of each cell line was also calculated. FIG. 9 shows the SPR of CHOS, CHOSX and CHOSXE cell lines in µg/1×$10^6$ cells/day between day 4 and day 7. Specific productivity rate per cell was clearly higher in CHOSXE compared to either CHOS or CHOSX cell lines.

Figure 10:
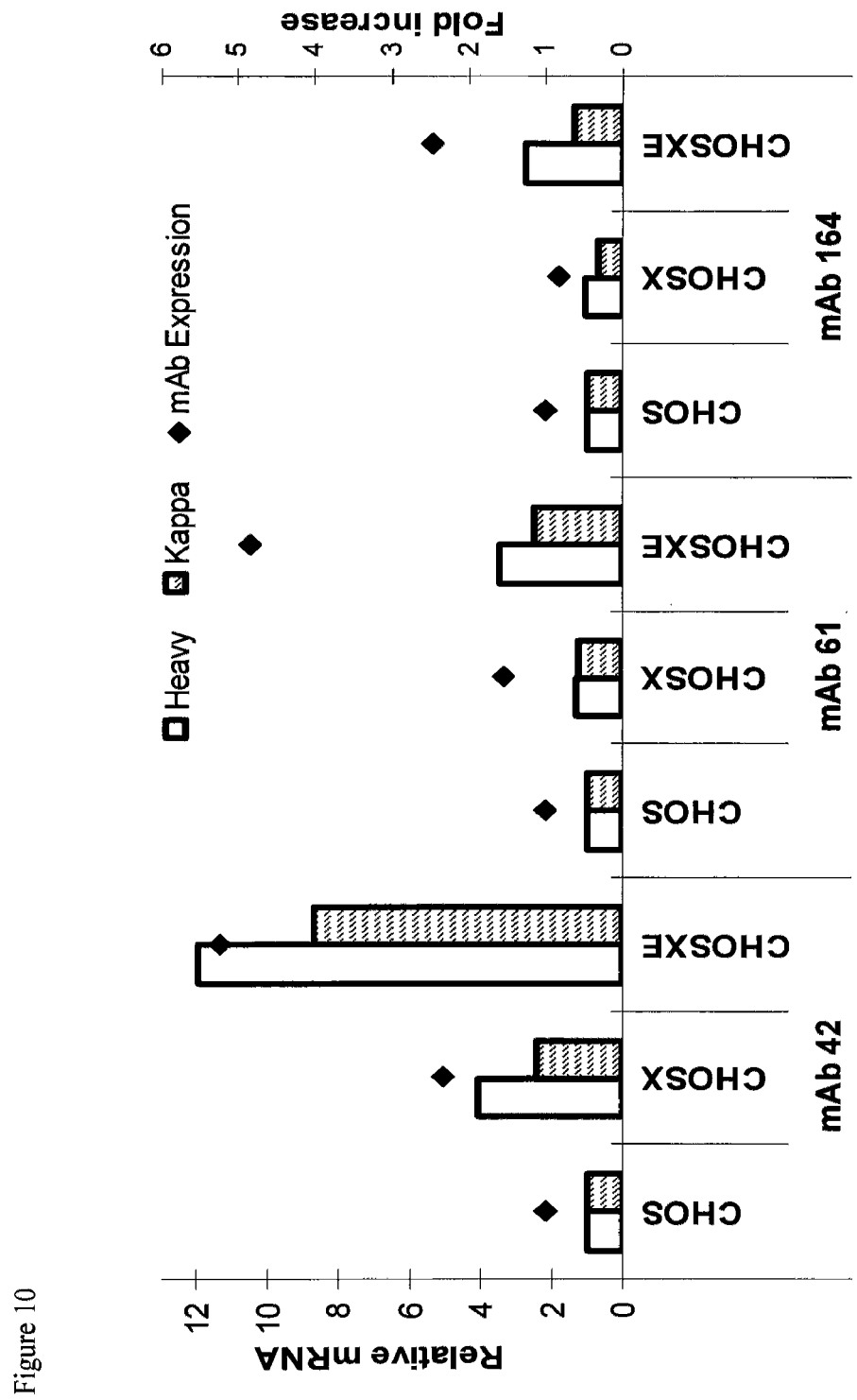
FIG. 10 shows the relative heavy chain and kappa light chain mRNA expression for antibodies 42, 61 and 164 expressed in CHOSX and CHOSXE cell lines compared to CHOS cell line.

The relative mRNA levels of heavy and kappa light chains of the mAbs 42, 61 and 164 were also measured by real time PCR (Taqman). The results are shown in FIG. 10, it can be seen that CHOSXE produced higher levels of the heavy and light chain mRNA compared to CHOS and CHOSX.

Example 6

Electroporation of Antibodies into CHOSXE, CHOSX, CHOS and CHOK1 Cell Lines and Subsequent Purification CHOS, CHOSX, CHOSXE and CHOK1 cells were transfected as outlined in example 5.

Figure 11:
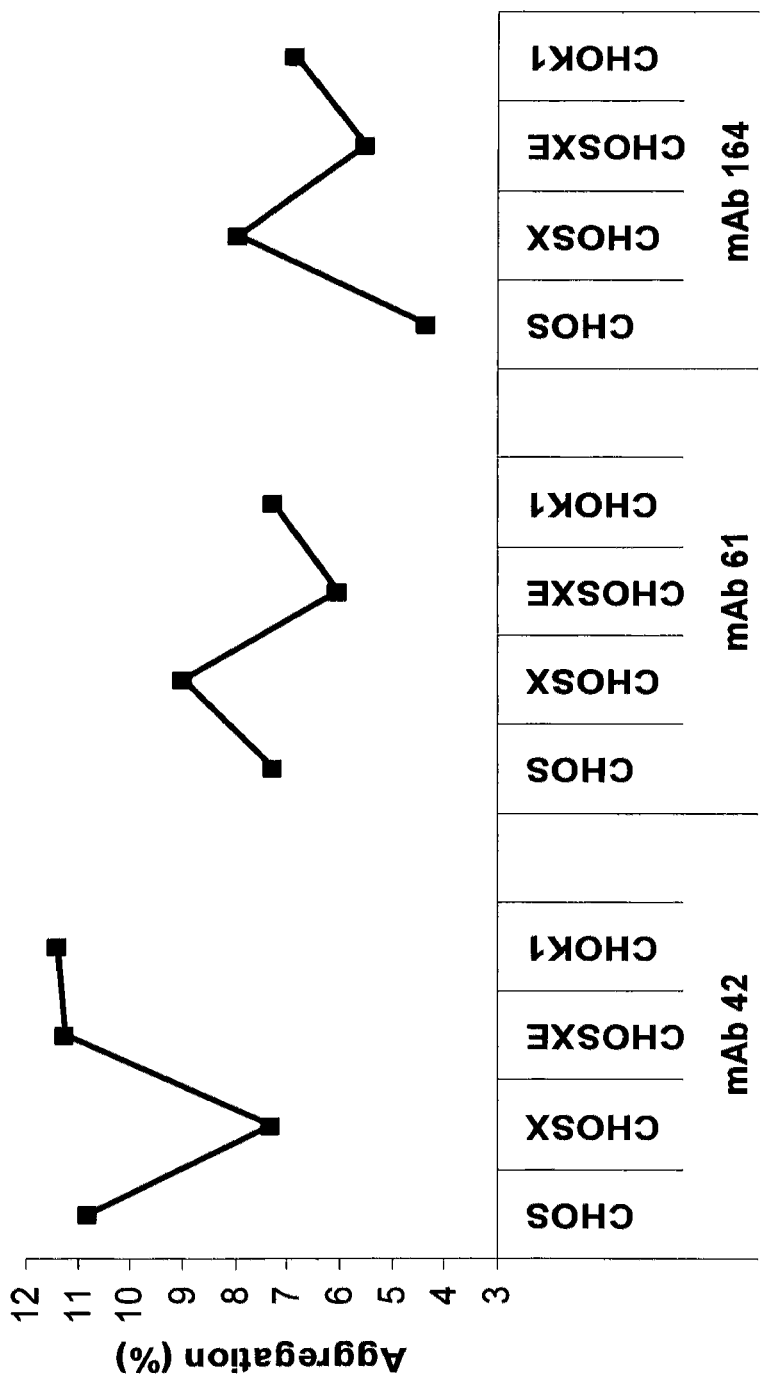
FIG. 11 shows the % aggregation of antibodies 42, 61 and 164 expressed in CHOK1, CHOS, CHOSX and CHOSXE.

MAb quantification was done by high-performance liquid affinity chromatography (HPLC) utilizing Protein G as a ligand. A standard curve was generated by injecting known amounts of purified IgG and analyzing the elution peaks. mAb eluate was monitored at 280 nm and extrapolated from the standard curve to calculate the mAbs' concentrations using their respective extinction coefficients (concentration=absorbance/extinction coefficient) (Table 1).

mAbs were purified using MabSelect Sure columns. The protein-A derived MabSelect Sure ligand is derived from *E. coli* and has been engineered to create an affinity medium with enhanced alkali stability and high binding capacity for IgG. At this point a trace HPLC was done to determine the percentage aggregate of the affinity-purified pooled fractions. The degree of aggregation exhibited by mAbs expressed in CHOSXE was comparable to CHOS, CHOSX and CHOK1 (see FIG. 11). Following MabSelect Sure, antibodies were further purified using size exclusion HPLC. The total mAb yield post-purification was also determined by reading absorbance of the mAb at 280 nm and calculating concentration as above.

Table 3 shows increases in antibody concentration relative to the CHOS cells after prot G HPLC and protein purification.

TABLE 3

| | | Fold increase | |
|---|---|---|---|
| | | Prot G HPLC | Yield after Purification |
| Ab42 | CHOS | 1.00 | 1.00 |
| | CHOSX | 1.09 | 0.83 |
| | CHOSXE | 6.28 | 7.22 |
| | CHOK1 | 1.65 | 2.70 |
| Ab61 | CHOS | 1.00 | 1.00 |
| | CHOSX | 2.39 | 3.30 |
| | CHOSXE | 5.36 | 5.24 |
| | CHOK1 | 1.58 | 2.35 |
| Ab164 | CHOS | 1.00 | 1.00 |
| | CHOSX | 2.68 | 2.44 |
| | CHOSXE | 5.94 | 6.14 |
| | CHO K1 | 1.94 | 2.80 |

It can be seen from Table 3 that the CHOSXE cells produced a significantly higher quantity of antibody compared to CHOS, CHOSX and CHOK1 cells.

Example 7

Antibody Quality Analysis

Purified mAbs from CHOSXE cells were analyzed for quality and activity as described below.
Sodium Dodecyl Sulfate Polyarcylamide Gel Electrophoresis (SDS PAGE)

Figure 12A:
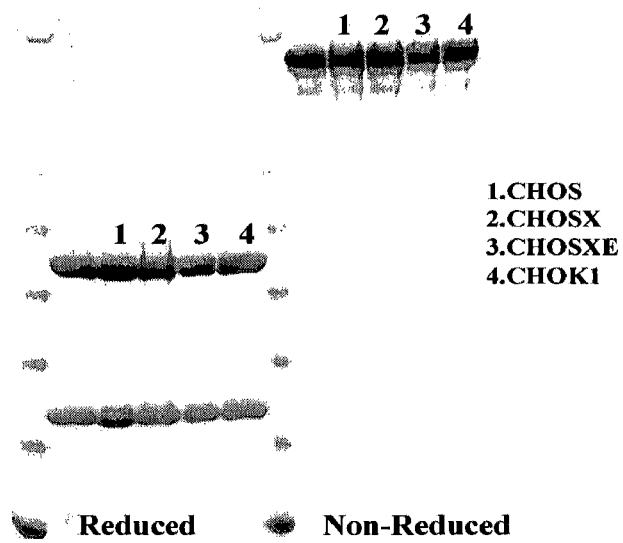
FIG. 12*a* shows an SDS PAGE of antibody 42 expressed in CHOS, CHOSX CHOSXE and CHOK1.
Figure 12B:
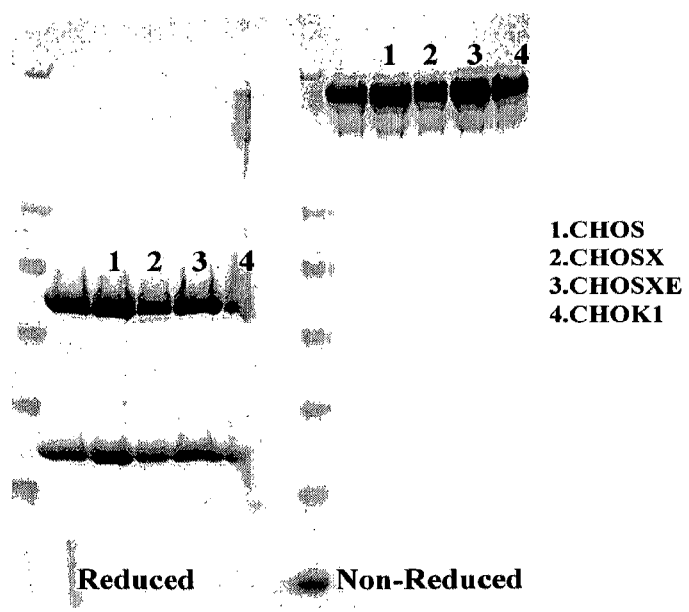
FIG. 12*b* shows an SDS PAGE of antibody 61 expressed in CHOS, CHOSX CHOSXE and CHOK1.
Figure 12C:
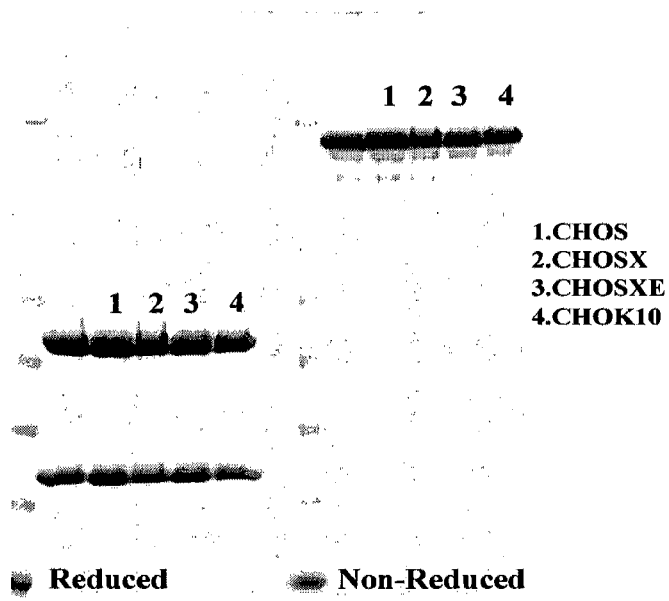
FIG. 12*c* shows an SDS PAGE of antibody 164 expressed in CHOS, CHOSX CHOSXE and CHOK1.
Figure 13:
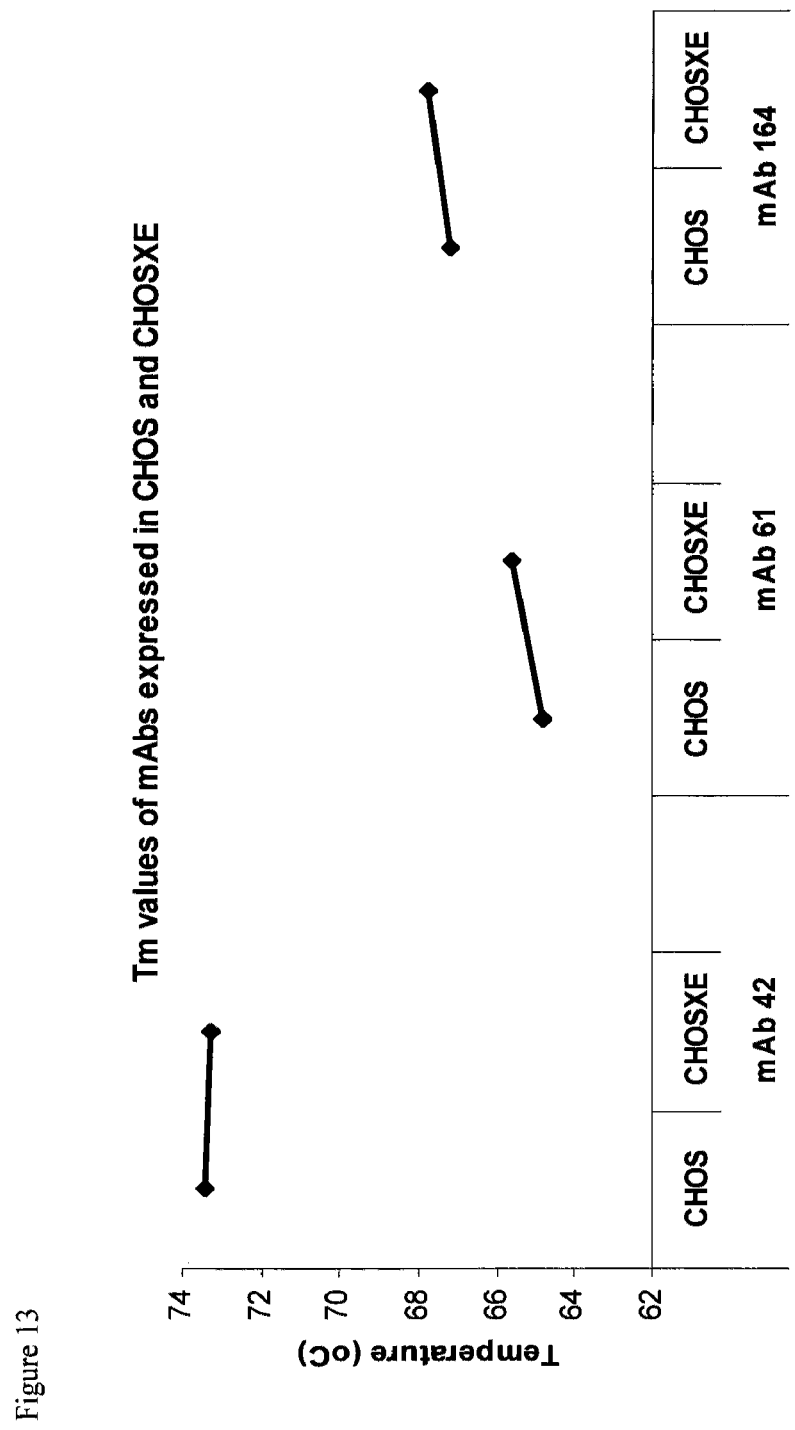
FIG. 13 shows the results from a thermofluor assay of antibodies 42, 61 and 164 expressed in CHOS and CHOSXE.

MAbs 42, 61 and 164 were analyzed by SDS PAGE to determine whether the expressed antibody was of the expected size. The SDS PAGE analysis was performed by running 5 µg of reduced and non-reduced protein on a pre-packed 4-12% Bis-Tris gradient gel (Invitrogen) at 50 mA for 45 minutes. FIGS. 12a, b and c show the results of the SDS PAGE, it can be seen that the antibodies were the same size whether expressed from CHOS, CHOSX, CHOSXE or CHOK1.
Thermofluor Assay The thermostability of MAbs 42, 61 and 164 were analyzed in a Thermofluor assay. This assay allows one to determine at which temperature the protein structure becomes unfolded. An environmentally sensitive fluorescent dye was used to monitor the thermal unfolding process of the proteins. The dye binds hydrophobic regions that become exposed upon unfolding and changes its emission spectrum. 1 µl of sample at 1 mg/ml, 1 µl of 30× dye, and 8 µl of buffer was placed into a well of a 384 PCR optical well plate (samples run in quadruplicate). 7900HT fast real-time PCR system contains a heating device for accurate temperature control set at 20° C. to 99° C., a CCD device simultaneously monitors the fluorescence changes in the wells. Standard deviations were less than 0.5° C., for the thermofluor assay data presented. The results from the Thermofluor assay are shown in FIG. 13 where it can be seen that there were no significant differences between the thermostability properties of mAbs when expressed from CHOS or CHOSXE.
Iso-Electric Focussing MAb 42, 61 and 164 were analyzed by Iso-electric focussing to determine if the expressed antibodies had the same net charge. High voltage was applied across the capillary using anode and cathode, which were dipped, in small reservoirs containing catholyte (OH⁻) and anolyte (H⁺). Samples were prepared with carrier ampholytes and on application of high voltage the protein molecules migrated and focused according to their respective pIs. The system used was the iCE 280 from Convergent biosciences (Isogen in Europe) which is an imaged capillary isoelectrophoresis instrument used to determine pIs of various protein samples and their related species. The results showed no major differences between the charges antibodies expressed in CHOK1SV, CHOS and CHOSXE.

Mass Spectrometry

The glycosylation profiles of mAbs 42, 61 and 164 were analyzed by mass spectrometry. 100 µg of each sample was treated with PNGase under native conditions to release N-glycans. Glycan separated from deglycosylated protein by SEC and the glycan fraction was analysed by MALDI Mass Spec. This analysis determined if the expressed antibodies had the same glycosylation profiles and whether any unfavourable sugar moieties had bound to the antibodies. The results from the glycosylation profiles are shown in FIG. 14 show that there were no significant differences between the glycosylation profiles of the antibodies expressed from CHOS and CHOSXE.

Antigen Binding Assay

Figure 15:
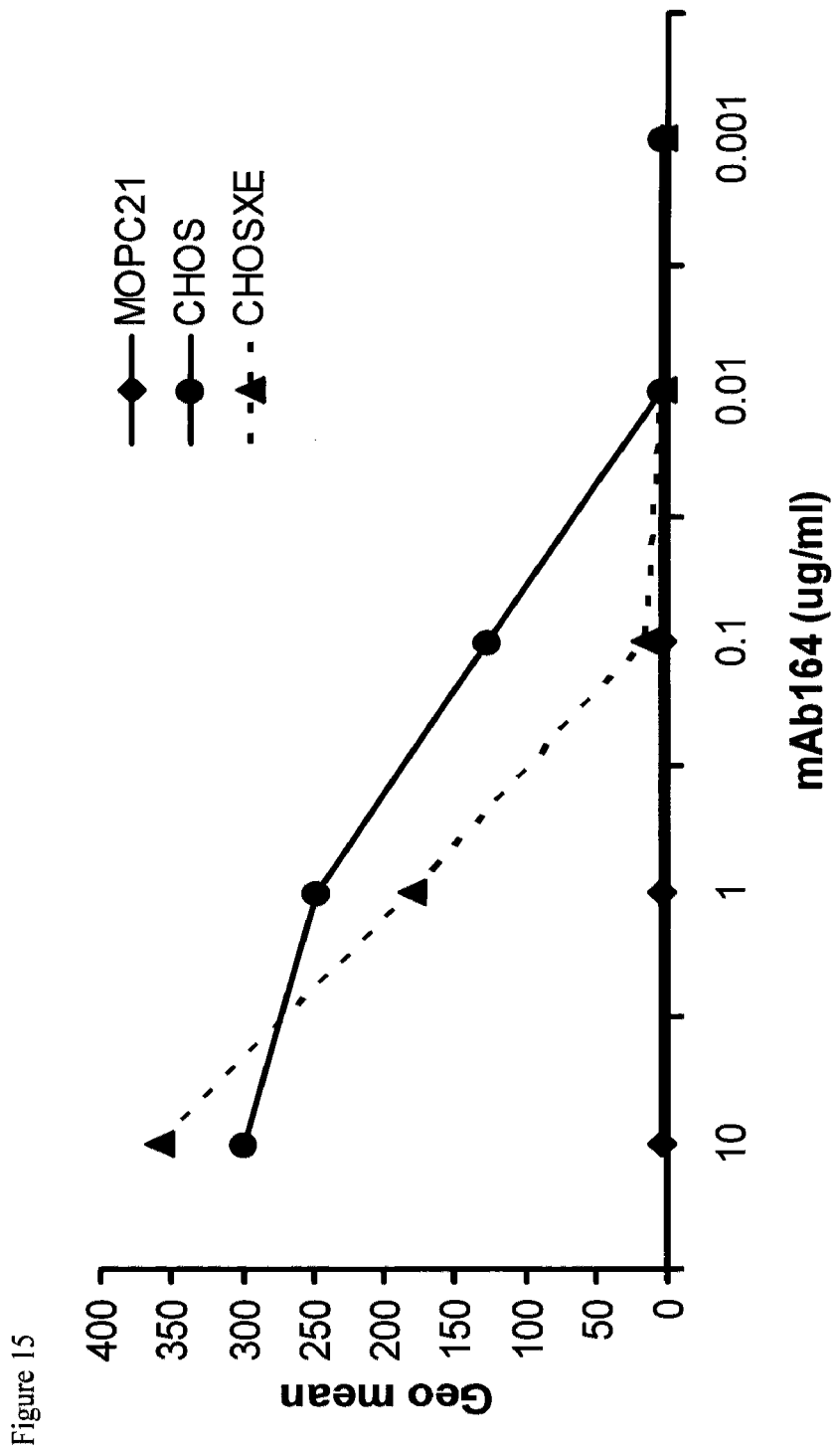
FIG. 15 shows the results from an antigen binding assay of 164 expressed in CHOS and CHOSXE.

MAb164 was analyzed in an antigen binding assay to determine if the expressed antibody had the same antigen binding affinity. BALB/C splenocytes expressing the target antigen of mAb 164 were treated with a titration of mAb 164. Cells were washed and treated with a PE labeled anti-mouse IgG1. Fluorescence cell staining was determined using FACS. The results from the assay are shown in FIG. 15 where "Geo mean" is the geometric mean value of fluorescence of antibody binding. MOPC21 is anti-mouse IgG1 antibody and used as a negative control. FIG. 15 shows that mAb 164 expressed from CHOSXE did not have significantly different antigen binding activity compared to the antibody expressed from CHOS.

In view of the above, it is clear that the antibodies expressed from CHOSXE did not exhibit any major differences from the antibodies expressed from other cell lines. Accordingly, the cell according to the present invention is capable of expressing a protein of interest, such as an antibody, having the same properties compared to when the protein is expressed in other cells, specifically cells which have not been modified to over express Ero1 and XBP1.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. An in vitro recombinant host cell, wherein the cell is modified to comprise (a) an exogenous polynucleotide sequence encoding Endoplasmic Reticulum Oxidoreductin 1 (Ero1) or a variant thereof which retains at least 80% of the activity of an endogenous Ero1, and (b) an exogenous polynucleotide sequence encoding X-box binding protein 1 (XBP1) or a variant thereof which retains at least 80% of the activity of the endogenous XBP1, wherein said modified host cell has increased expression levels of Ero1 and XBP1 relative to the expression levels of Ero1 and XBP1 in an unmodified cell of the same type.

2. The cell according to claim 1, wherein the cell comprises an exogenous polynucleotide encoding Ero1 and XBP1, the Ero1 variant and XBP1, Ero1 and the XBP1 variant, or the Ero1 variant and the XBP1 variant.

3. The cell according to claim 2, wherein the cell comprises an expression cassette comprising the Ero1 and XBP1 polynucleotide.

4. The cell according to claim 2, wherein the cell comprises a vector comprising the Ero1 and XBP1 polynucleotide.

5. The cell according to claim 1, wherein the cell comprises a first expression cassette comprising the Ero1 polynucleotide and a second expression cassette comprising the XBP1 polynucleotide.

6. The cell according to claim 1, wherein the cell comprises first vector comprising the Ero1 polynucleotide and a second vector comprising the XBP1 polynucleotide.

7. The cell according to claim 1, wherein the polynucleotide sequence encoding Ero1 encodes Ero1α or Ero1β.

8. The cell according to claim 7, wherein the polynucleotide sequence encoding Ero1 encodes Ero1α and comprises the sequence given in SEQ ID NO: 4.

9. The cell according to claim 7, wherein the polynucleotide sequence encoding Ero1 encodes the polypeptide sequence given in SEQ IDNO: 3.

10. The cell according to any claim 1, wherein the polynucleotide sequence encoding XBP1 comprises the sequence given in SEQ ID NO: 2.

11. The cell according to claim 1, wherein the polynucleotide sequence encoding XBP1 encodes the polypeptide sequence given in SEQ IDNO: 1.

12. The cell according to claim 1, wherein the cell further comprises a polynucleotide sequence encoding a protein of interest, wherein the protein of interest is exogenous.

13. The cell according to claim 12, wherein the polynucleotide sequence encoding the protein of interest is within an expression cassette or a vector that does not comprise nucleic acid sequence encoding XBP1, Ero1, or a combination thereof.

14. The cell according to claim 12, wherein the protein of interest is an antibody or an antigen binding fragment thereof.

15. The cell according to claim 1, wherein the cell is further modified to increase the expression levels of a further component of the unfolded protein response (UPR) pathway relative to the expression levels of the further component of the UPR pathway in an unmodified cell not having increased expression of the further component of the UPR pathway.

16. The cell according to claim 15, wherein the cell further comprises an exogenous polynucleotide sequence encoding the component of the unfolded protein response (UPR) pathway.

17. The cell according to claim 1, wherein the cell is a mammalian cell.

18. The cell according to claim 17, wherein the cell is a CHO cell.

19. The cell of claim 18, wherein said cell is from a CHO-SXE cell line as deposited at the European Collection of Cell Cultures (ECACC) the Accession number: 10021001.

20. A method for modifying a host cell in vitro to increase the capability of the host cell to express (a) Ero1 polypeptide or a variant thereof which retains at least 80% of the activity of an endogenous Ero1 and (b) XBP1 polypeptide or a variant thereof which retains at least 80% of the activity of an endogenous XBP1 in the host cell at expression levels greater than the expression levels of Ero1 and XBP1 in an unmodified cell of the same type, wherein the method comprises transfecting the cell with one or more polynucleotides, one or more expression cassettes, and/or one or more vectors comprising (i) an exogenous polynucleotide sequence encoding Ero1 or a variant thereof which retains at least 80% of the activity of an endogenous Ero1 and (ii) an exogenous polynucleotide sequence encoding XBP1 or a variant thereof which retains at least 80% of the activity of an endogenous XBP1.

21. The method according to claim 20, wherein the method comprises a further step of culturing the modified cell in a medium to thereby express increased levels of Ero1 polypeptide or a variant thereof which retains at least 80% of the activity of an endogenous Ero1; and XBP1 polypeptide or a variant thereof which retains at least 80% of the activity of an endogenous XBP1 compared to an unmodified cell.

22. The method according to claim 21, wherein the method further comprises the following steps:
  (a) selecting one or more modified cell clones;
  (b) measuring the quantity of Ero1 mRNA and/or protein in the selected one or more cell clones; and
  (c) measuring the quantity of XBP1 mRNA and/or protein in the selected one or more clones.

23. The method according to claim 22, wherein the method further comprises the following steps:
  (a) comparing the quantity of Ero1 mRNA and/or protein and XBP1 mRNA and/or protein in the modified cell clones to the quantity of Ero1 mRNA and/or protein and XBP1 mRNA and/or protein in an unmodified cell clone; and
  (b) selecting one or more modified cell clones having a higher quantity of Ero1 mRNA and/or protein and XBP1 mRNA and/or protein compared to the unmodified cell clone.

24. The method according to claim 20, wherein the method further comprises transfecting the host cell with a polynucleotide sequence encoding a protein of interest and expressing the protein of interest.

25. The method according to claim 20, wherein the method further comprises increasing the expression levels of a further component of the unfolded protein response pathway (UPR)

in the modified cells relative to the expression levels of the further component of the UPR pathway in an unmodified cell.

26. The method according to claim 25, wherein the modified host cell further comprises an exogenous polynucleotide sequence encoding the further component of the unfolded protein response (UPR) pathway.

27. A method of producing a recombinant protein of interest comprising expressing the recombinant protein of interest in a cell of claim 12.

* * * * *

SEQUENCE LISTING

```
<160> NUMBER OF SEQ ID NOS: 4

<210> SEQ ID NO 1
<211> LENGTH: 376
<212> TYPE: PRT
<213> ORGANISM: Homo sapiens

<400> SEQUENCE: 1

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175
```

```
His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
            195                 200                 205

Lys Cys Pro Ser Pro Glu Pro Ala Ser Leu Glu Glu Leu Pro Glu Val
        210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Val Lys Ile Glu Glu Ala Pro Leu Ser
        275                 280                 285

Pro Ser Glu Asn Asp His Pro Glu Phe Ile Val Ser Val Lys Glu Glu
    290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375

<210> SEQ ID NO 2
<211> LENGTH: 1132
<212> TYPE: DNA
<213> ORGANISM: Homo sapiens

<400> SEQUENCE: 2
aatggtggtg gtggcagccg cgccgaaccc ggccgacggg accectaaag ttctgcttct    60 gtcgggcag cccgcctccg ccgccggagc cccggccggc caggccctgc cgctcatggt    120
gccagcccag agaggggcca gccggaggc agcgagcggg gggctgcccc aggcgcgcaa    180
gcgacagcgc ctcacgcacc tgagccccga ggagaaggcg ctgaggagga aactgaaaaa    240
cagagtagca gctcagactg ccagagatcg aaagaaggct cgaatgagtg agctggaaca    300
gcaagtggta gatttagaag aagagaacca aaaacttttg ctagaaaatc agcttttacg    360
agagaaaact catggccttg tagttgagaa ccaggagtta agacagcgct tggggatgga    420
tgccctggtt gctgaagagg aggcggaagc caaggggaat gaagtgaggc cagtggccgg    480
gtctgctgag tccgcagcag gtgcaggccc agttgtcacc cctccagaac atctccccat    540
ggattctggc ggtattgact cttcagattc agagtctgat atcctgttgg gcattctgga    600
caacttggac ccagtcatgt tcttcaaatg cccttcccca gagcctgcca gctggagga    660 gctcccagag gtctacccag aaggacccag ttccttacca gcctcccttt ctctgtcagt    720
ggggacgtca tcagccaagc tggaagccat taatgaacta attcgttttg accacatata    780
taccaagccc ctagtcttag ataccectg tgagacagag agccaagcta atgtggtagt    840
gaaaatcgag gaagcaccctc tcagcccctc agagaatgat caccctgaat tcattgtctc    900
agtgaaggaa gaacctgtag aagatgacct cgttccggag ctgggtatct caaatctgct    960
```

-continued

```
ttcatccagc cactgcccaa agccatcttc ctgcctactg gatgcttaca gtgactgtgg    1020
atacgggggt tccctttccc cattcagtga catgtcctct ctgcttggtg taaaccattc    1080
ttgggaggac acttttgcca atgaactctt tccccagctg attagtgtct aa            1132
```

<210> SEQ ID NO 3
<211> LENGTH: 468
<212> TYPE: PRT
<213> ORGANISM: Homo sapiens

<400> SEQUENCE: 3

```
Met Gly Arg Gly Trp Gly Phe Leu Phe Gly Leu Leu Gly Ala Val Trp
1               5                   10                  15

Leu Leu Ser Ser Gly His Gly Glu Glu Gln Pro Pro Glu Thr Ala Ala
            20                  25                  30

Gln Arg Cys Phe Cys Gln Val Ser Gly Tyr Leu Asp Asp Cys Thr Cys
        35                  40                  45

Asp Val Glu Thr Ile Asp Arg Phe Asn Asn Tyr Arg Leu Phe Pro Arg
    50                  55                  60

Leu Gln Lys Leu Leu Glu Ser Asp Tyr Phe Arg Tyr Tyr Lys Val Asn
65                  70                  75                  80

Leu Lys Arg Pro Cys Pro Phe Trp Asn Asp Ile Ser Gln Cys Gly Arg
                85                  90                  95

Arg Asp Cys Ala Val Lys Pro Cys Gln Ser Asp Glu Val Pro Asp Gly
            100                 105                 110

Ile Lys Ser Ala Ser Tyr Lys Tyr Ser Glu Glu Ala Asn Asn Leu Ile
        115                 120                 125

Glu Glu Cys Glu Gln Ala Glu Arg Leu Gly Ala Val Asp Glu Ser Leu
    130                 135                 140

Ser Glu Glu Thr Gln Lys Ala Val Leu Gln Trp Thr Lys His Asp Asp
145                 150                 155                 160

Ser Ser Asp Asn Phe Cys Glu Ala Asp Asp Ile Gln Ser Pro Glu Ala
                165                 170                 175

Glu Tyr Val Asp Leu Leu Leu Asn Pro Glu Arg Tyr Thr Gly Tyr Lys
            180                 185                 190

Gly Pro Asp Ala Trp Lys Ile Trp Asn Val Ile Tyr Glu Glu Asn Cys
        195                 200                 205

Phe Lys Pro Gln Thr Ile Lys Arg Pro Leu Asn Pro Leu Ala Ser Gly
    210                 215                 220

Gln Gly Thr Ser Glu Glu Asn Thr Phe Tyr Ser Trp Leu Glu Gly Leu
225                 230                 235                 240

Cys Val Glu Lys Arg Ala Phe Tyr Arg Leu Ile Ser Gly Leu His Ala
                245                 250                 255

Ser Ile Asn Val His Leu Ser Ala Arg Tyr Leu Leu Gln Glu Thr Trp
            260                 265                 270

Leu Glu Lys Lys Trp Gly His Asn Ile Thr Glu Phe Gln Gln Arg Phe
        275                 280                 285

Asp Gly Ile Leu Thr Glu Gly Glu Gly Pro Arg Arg Leu Lys Asn Leu
    290                 295                 300

Tyr Phe Leu Tyr Leu Ile Glu Leu Arg Ala Leu Ser Lys Val Leu Pro
305                 310                 315                 320

Phe Phe Glu Arg Pro Asp Phe Gln Leu Phe Thr Gly Asn Lys Ile Gln
                325                 330                 335

Asp Glu Glu Asn Lys Met Leu Leu Leu Glu Ile Leu His Glu Ile Lys
```

```
                340             345             350
Ser Phe Pro Leu His Phe Asp Glu Thr Ser Phe Phe Ala Gly Asp Lys
            355                 360                 365

Lys Glu Ala His Lys Leu Lys Glu Asp Phe Arg Leu His Phe Arg Asn
        370                 375                 380

Ile Ser Arg Ile Met Asp Cys Val Gly Cys Phe Lys Cys Arg Leu Trp
385                 390                 395                 400

Gly Asn Leu Gln Thr Gln Gly Leu Gly Thr Ala Leu Lys Ile Leu Phe
                405                 410                 415

Ser Glu Lys Leu Ile Ala Asn Met Pro Glu Ser Gly Pro Ser Tyr Glu
            420                 425                 430

Phe His Leu Thr Arg Gln Glu Ile Val Ser Leu Phe Asn Ala Phe Gly
        435                 440                 445

Arg Ile Ser Thr Ser Val Lys Glu Leu Glu Asn Phe Arg Asn Leu Leu
    450                 455                 460

Gln Asn Ile His
465

<210> SEQ ID NO 4
<211> LENGTH: 1407
<212> TYPE: DNA
<213> ORGANISM: Homo sapiens

<400> SEQUENCE: 4
atgggccgcg gctggggatt cttgtttggc ctcctgggcg ccgtgtggct gctcagctcg     60
ggccacggag aggagcagcc cccggagaca gcggcacaga ggtgcttctg ccaggttagt    120
ggttacttgg atgattgtac ctgtgatgtt gaaaccattg atagatttaa taactacagg    180
cttttcccaa gactacaaaa acttcttgaa agtgactact ttaggtatta caaggtaaac    240
ctgaagaggc cgtgtccttt ctggaatgac atcagccagt gtggaagaag ggactgtgct    300
gtcaaaccat gtcaatctga tgaagttcct gatggaatta aatctgcgag ctacaagtat    360
tctgaagaag ccaataatct cattgaagaa tgtgaacaag ctgaacgact tggagcagtg    420
gatgaatctc tgagtgagga aacacagaag gctgttcttc agtggaccaa gcatgatgat    480
tcttcagata acttctgtga agctgatgac attcagtccc ctgaagctga atatgtagat    540
ttgcttctta atcctgagcg ctacactggt tacaagggac agatgcttg aaaatatgg     600 aatgtcatct acgaagaaaa ctgttttaag ccacagacaa ttaaaagacc tttaaatcct    660
ttggcttctg gtcaagggac aagtgaagag aacactttt acagttggct agaaggtctc    720
tgtgtagaaa aaagagcatt ctacagactt atatctggcc tacatgcaag cattaatgtg    780
catttgagtg caagatatct tttacaagag acctggttag aaaagaaatg ggacacaac     840 attacagaat tcaacagcg atttgatgga atttgactg aaggagaagg tccaagaagg    900
cttaagaact tgtattttct ctacttaata gaactaaggg ctttatccaa agtgttacca    960
ttcttcgagc gcccagattt tcaactcttt actggaaata aaattcagga tgaggaaaac   1020
aaaatgttac ttctggaaat acttcatgaa atcaagtcat ttcctttgca ttttgatgag   1080
acttcatttt ttgctgggga taaaaagaa gcacacaaac taaggagga ctttcgactg    1140 cattttagaa atatttcaag aattatggat tgtgttggtt gttttaaatg tcgtctgtgg   1200
ggaaatcttc agactcaggg tttgggcact gctctgaaga tcttattttc tgagaaattg   1260
atagcaaata tgccagaaag tggacctagt tatgagttcc atctaaccag acaagaaata   1320
```

```
gtatcattat tcaacgcatt tggaagaatt tctacaagtg tgaaagaatt agaaaacttc    1380
aggaacttgt tacagaatat tcattaa                                        1407
```